(12) United States Patent
McGinley et al.

(10) Patent No.: US 11,950,815 B2
(45) Date of Patent: Apr. 9, 2024

(54) VARIABLE ANGLE ORTHOPEDIC FASTENERS FOR FIXATION OF AN ORTHOPEDIC IMPLANT

(71) Applicant: McGinley Engineered Solutions, LLC, Casper, WY (US)

(72) Inventors: Joseph C. McGinley, Casper, WY (US); Vincent Palazzolo, Casper, WY (US); Ben Warren, Casper, WY (US); Adam Johnson, Casper, WY (US)

(73) Assignee: MCGINLEY ENGINEERED SOLUTIONS, LLC, Casper, WY (US)

( * ) Notice: Subject to any disclaimer, the term of this patent is extended or adjusted under 35 U.S.C. 154(b) by 94 days.

(21) Appl. No.: 17/731,042

(22) Filed: Apr. 27, 2022

(65) Prior Publication Data

US 2022/0280210 A1 Sep. 8, 2022

Related U.S. Application Data

(63) Continuation of application No. 16/628,638, filed as application No. PCT/US2018/033730 on May 21, 2018, now Pat. No. 11,337,738.

(60) Provisional application No. 62/509,279, filed on May 22, 2017.

(51) Int. Cl.
*A61B 17/86* (2006.01)
*A61B 17/80* (2006.01)

(52) U.S. Cl.
CPC ...... *A61B 17/8047* (2013.01); *A61B 17/8605* (2013.01); *A61B 17/8685* (2013.01)

(58) Field of Classification Search
CPC ............ A61B 17/8605; A61B 17/8047; A61B 17/8042; A61B 17/8085
See application file for complete search history.

(56) References Cited

U.S. PATENT DOCUMENTS

| | | | |
|---|---|---|---|
| 5,902,303 A | 5/1999 | Eckhof et al. | |
| 6,605,090 B1 | 8/2003 | Trieu | |
| 2008/0119895 A1 | 5/2008 | Manceau | |
| 2012/0089192 A1 | 4/2012 | Biedermann | |
| 2013/0190825 A1* | 7/2013 | Perrow | A61B 17/861 606/305 |
| 2013/0317554 A1 | 11/2013 | Purcell | |
| 2014/0277179 A1 | 9/2014 | Ziolo | |
| 2015/0182272 A1* | 7/2015 | Weiman | A61B 17/861 606/300 |
| 2015/0320462 A1 | 11/2015 | Biedermann | |
| 2017/0265914 A1 | 9/2017 | Wiederkehr | |

FOREIGN PATENT DOCUMENTS

| | | |
|---|---|---|
| EP | 1458299 A1 | 9/2004 |
| KR | 20120082397 | 7/2012 |
| KR | 2014003111 | 5/2014 |

* cited by examiner

*Primary Examiner* — Olivia C Chang
(74) *Attorney, Agent, or Firm* — HOLZER PATEL DRENNAN

(57) ABSTRACT

Systems for variable angle insertion of surgical fasteners relative to an orthopedic plate with locking of the surgical fastener relative to the plate upon insertion. The systems may include a pivot member secured relative to either the orthopedic plate or the fastener. In either regard, the pivot member may provide locking engagement with the plate to lockingly engage the fastener relative to the plate.

13 Claims, 21 Drawing Sheets

VARIABLE ANGLE ORTHOPEDIC FASTENERS FOR FIXATION OF AN ORTHOPEDIC IMPLANT

RELATED APPLICATIONS

This application is a continuation of U.S. application Ser. No. 16/628,638 filed on Jan. 3, 2020, entitled "VARIABLE ANGLE ORTHOPEDIC FASTENERS FOR FIXATION OF AN ORTHOPEDIC IMPLANT," which is a National Stage Application under 35 U.S.C. § 371 of International Application No. PCT/US2018/033730, filed on May 21, 2018, entitled "VARIABLE ANGLE ORTHOPEDIC FASTENERS FOR FIXATION OF AN ORTHOPEDIC IMPLANT," which claims the benefit of U.S. Provisional Patent Application No. 62/509,279 filed May 22, 2017, entitled "VARIABLE ANGLE ORTHOPEDIC FASTENERS FOR FIXATION OF AN ORTHOPEDIC IMPLANT," which is incorporated herein by reference in its entirety.

FIELD

The present disclosure generally relates to orthopedic hardware, and in particular to plates and screws for fixation of orthopedic hardware relative to the bone of a patient.

BACKGROUND

In many orthopedic surgeries, various types of hardware may be affixed to a bone of a patient. For instance, orthopedic plates may be used for fixation of bones that have been fractured. A variety of plate types may be provided for use in different contexts. In certain instances, a plate type may be particular to a given anatomical use and/or plate function. In any regard, most often such plates are affixed to the bone of a patient using surgical fasteners such as bone screws.

In some approaches to affixing an orthopedic plate to a bone, it may be desirable to provide flexibility in relation to the angle at which the fastener or screw used to secure the plate to the bone is disposed relative to the plate. For example, it may be desirable to allow for screws to be inserted at various different angles in relation to a plate for different plate applications. However, previously contemplated fasteners and fastener systems include drawbacks that limit the applicability and/or effectiveness of such systems when providing flexibility in relation to the angle at which a screw is advanced relative to a plate for securing a plate to a bone of a patient.

In this regard, a number of systems have been proposed to allow for a screw to be inserted at variable different angles relative to the plate. In such contexts, it may be desirable to provide locking screws that include head portions that are secured to the plate upon insertion of the screw into the bone. As will be seen in the discussion below, provision of a locking screw system that is efficient to use, allows for variable angulation of the screw relative to the plate, and provides for good patient outcomes has yet to be adequately provided.

Some proposed systems include multiple, separately provided pieces that must be manipulated and arranged by the surgeon prior to or at the time of screw insertion. In this regard, the surgeon is required to manipulate a number of parts in relation to screw insertion, which may be particularly difficult when screw insertion is provided in awkward positions relative to the anatomy of the patient. Moreover, the potential for loss of one or more of these parts exists, which may increase foreign body exposure in the surgical site.

In other proposed approaches, the plate through which the screw passes during insertion may comprise a relatively softer material than the screw. In this regard, the screw head is provided with threads that cut into the plate to tap threads as the screw is advanced relative to the plate, thus locking the screw to the plate. That is, the screw may provide self-tapping of the relatively softer material to engage the plate to lock the screw to the plate. However, in this approach, the potential for metal shavings to be produced as the screw head self-taps to the plate. While efforts may be undertaken to remove such metal shavings, any remaining shavings may remain that may result in soft tissue damage. Moreover, after insertion (e.g., during the healing process), this approach may result in cold fusion to occur between the screw head and the plate. In turn, when removing the plate, it may be necessary to use alternative techniques for screw removal other than simply unscrewing the screw from the plate and bone. For instance, the screw may be required to be drilled to remove the screw from the plate and a complicated screw removal process may be undertaken.

SUMMARY

In view of the foregoing, improved orthopedic hardware systems are needed that facilitate variability in relation to the angle at which fasteners are advanced relative to a plate to secure the plates to a bone of the patient. Specifically, a persistent need exists in orthopedic systems that allows for a screw to be used to secure a plate to a bone such that the screw may be positioned with variable angulation relative to the plate in a manner that is functional, efficient, safe, and allows screw removal.

Specifically, embodiments described herein may facilitate locking a fastener to a plate such that the fastener may be positioned in different relative angles relative to the plate. In turn, a pivot member may be provided that facilitates locking interaction between a fastener and a plate. However, unlike previous systems in which a separate component is provided to facilitate such locking interaction, the present disclosure contemplates an efficient, easy to use system in which components are secured so as to provide a traditional workflow during surgery. That is, the pivot member may be restrainedly engaged with the plate or the fastener such that a surgeon need not separately manipulate a third component beyond the plate and fastener.

In at least some of the embodiments described herein, when a fastener has been used for fixation of a plate to a bone, the fastener may be locked to the pivot member that is in turn locked to the plate. For instance, the fastener may include threads on a head portion thereof that engage corresponding threads provided on the pivot member. Accordingly, the threaded engagement between the head portion of the fastener and the pivot member may result in locking interaction between the pivot member and the fastener. In addition, the head portion engaging the pivot member may result in radial expansion of the pivot member, which may frictionally engage a sidewall of an aperture in the plate to lock the pivot member with respect to the plate. In this embodiment, the fastener may engage the bone of a patient and the plate so that the plate is not loaded in compression relative to the bone of the patient. In this regard, the resistance to shearing forces may be significantly improved. Specifically, when a locking screw that threadably engages the pivot member is used, the screw may be engaged with shearing forces along an entire length of the screw so as increase the resistance to shearing forces of the screw. In alternative embodiments, conventional screws may be used that load the pivot member and plate in compression for securing the plate relative to the bone of the patient.

In other embodiments, a fastener assembly may be provided in which the pivot member is securely retained relative to the fastener. In this regard, as the fastener is advanced relative to a plate for fixation of the plate relative to a bone of a patient, the pivot member may be disposed relative to the plate. Once the pivot member is disposed relative to the plate (e.g., relative to an aperture in the plate as a result of the advancement of the fastener relative thereto), the pivot member may lockingly engage the plate to secure the fastener relative to the plate.

Various approaches to locking the pivot member relative to the plate are described here. For instance, the pivot member may be configured relative to the fastener for co-rotation therewith. As an example, the pivot member may be correspondingly shaped relative to a non-circular profile of the fastener such that the pivot member co-rotates with the fastener. IN turn, upon rotational advancement of the fastener, the pivot member may also be rotated relative to the plate to engage locking features on the fastener and plate to lockingly engage the pivot member to the plate. Alternatively, the pivot member may be independently rotatable relative to the faster. As such, once the fastener is advanced relative to the plate, the pivot member may be independently rotated to engage locking features between the fastener and plate. Further still, the fastener may include features that allow for engagement of the pivot member to lockingly engage the fastener and pivot member to the plate. For instance, a head portion may be moveable to engage a ramped surface with the pivot member to radially expand the pivot member into frictional engagement with an aperture of the plate.

In view of the foregoing, a first aspect includes an orthopedic plate. The plate includes a plate body extending between an upper surface and a lower surface of the plate body. The plate also features an aperture extending through the plate body from the upper surface to the lower surface along a reference axis. The aperture has a sidewall extending circumferentially about an interior of the aperture. The plate includes a pivot member that is retained within the aperture. The pivot member includes an outer surface corresponding to the sidewall of the aperture. The pivot member defines a bore extending along a fastener insertion axis. The bore is configured to accept a fastener along the fastener insertion axis. In turn, the pivot member is disposable between a first configuration that allows relative movement between the outer surface and the sidewall and a second configuration in which the outer surface frictionally engages the sidewall to restrict movement of the pivot member relative to the aperture. The pivot member is displaceable relative to the plate body within the aperture when in the first configuration to define an included angle between the reference axis and the insertion axis.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, the second configuration of the pivot member may include radial expansion of the pivot member to frictionally engage the sidewall with the outer surface. In an embodiment, at least one of the bore or a head portion of the fastener disposed within the bore may include a sloped surface such that the head portion and the bore are engageable upon receipt of the fastener in the bore to cause the radial expansion. That is, the sloped surface of the head portion and/or bore may be disposed such that as the head portion is engaged with the pivot member (e.g., through threadable and/or compressive engagement), the pivot member may radially expand. As such, the pivot member may include an expansion slot that allows for the radial expansion of the pivot member radially relative to the fastener insertion axis. The expansion slot may extend through the pivot member in a direction along the insertion axis. In an embodiment, the slot may extend entirely through the pivot member in a direction along the insertion axis. That is, the pivot member may be split to facilitate radial expansion thereof. In other embodiments, a plurality of expansion slots may be provided that may be spaced about the pivot member. The plurality of expansion slots may extend partially through the pivot member to facilitate radial expansion of at least a portion of the pivot member.

In an embodiment, the aperture may include a non-circular sidewall portion and the outer surface of the pivot member may be engageable by the non-circular portion to inhibit rotation of the pivot member about the reference axis. As such, when the fastener is rotatable advanced relative to the pivot member, the pivot member may not rotate about the fastener insertion axis. The pivot member comprises a plurality of flats extending about the perimeter of the pivot member and the non-circular sidewall is correspondingly shaped flat portions. In an embodiment, the pivot member may be a substantially hexagonal member similar to commonly provided nuts. The aperture may include a ramped surface of a flange extending relative to the aperture that engages a convex portion of the pivot member. The pivot member may also include chamfers extending between the plurality of flats to facilitate unrestricted pivotal movement of the pivot member relative to the plate in two degrees of freedom. That is, in a traditional hexagonally shaped nut, pivotal movement within the aperture may be restricted due to interference between the flats of the nut and the sidewall. Providing chamfers between the flats of the pivot member may reduce or eliminate such interference, allowing the pivot member to pivot freely within the aperture.

In an embodiment, the plate may facilitate engagement of the fastener and the plate such that the fastener is loaded without compression forces. For instance, the bore may include threads adapted to engage corresponding threads on a head portion of the fastener. In this regard, by threadably engaging the pivot member with the head portion of the fastener, the fastener may be loaded without compression. It has been found that such absence of compression loading of a fastener may allow for greater resistance to shear forces or other forces (e.g., axial forces, tensile forces, bending moments, etc.) acting between the plate and the fastener as the plate is loaded (e.g., as a result of anatomical movement or the like).

In an embodiment, the included angle between the reference axis and the fastener insertion axis may be definable in at least one degree of freedom when the pivot member is in the first configuration. The included angle between the reference axis and the insertion axis may be definable in at least two degrees of freedom. The included angle between the reference axis and the fastener insertion axis is definable at any radial position about the reference axis. The included angle between the reference axis and the insertion axis may be at least about 10 degrees. Alternatively, the included angle between the reference axis and the insertion axis may be at least about 15 degrees.

The pivot member may be irremovably provided within the aperture. In this regard, the plate body may include extensions adjacent to the upper surface and extending relative to the aperture. The extensions may originally be positioned to allow for passage of the pivot member into the aperture. Thereafter, the extension members may be moved to secure the pivot member in the aperture. That is, the extensions may be displaceable into position to extend relative to the aperture upon receipt of the pivot member into the aperture to secure the pivot member within the aperture. As such, the extensions may extend relative to the aperture to retain the pivot member in the aperture. Such extensions may extend parallel to a surface of the plate or may extend in a direction normal to the surface of the plate. In this regard, the extensions may comprise flanges that extend normal to the surface of a plate to allow the pivot member to be disposed in the aperture, such that the flanges are moved into a parallel position relative to the surface of the plate to secure the pivot member. Alternatively, the extensions may extend parallel to the surface of the plate and define a hole through which the pivot member may be passed through in a collapsed or retracted state. Once through the hole and in the aperture, the pivot member may be expanded such that the extensions maintain the pivot member securely within the aperture.

A second aspect includes an orthopedic system for fixation of an orthopedic plate to a bone of a patient. The system may include a plate body extending between an upper surface and a lower surface of the plate body. An aperture may be provided that extends through the plate body from the upper surface to the lower surface along a reference axis. The aperture has a sidewall extending circumferentially about an interior of the aperture. The system also includes a pivot member retained within the aperture. The pivot member includes an outer surface corresponding to the sidewall. The pivot member also defines a bore extending along a fastener insertion axis. The pivot member is displaceable relative to the plate body within the aperture to define an included angle between the reference axis and the fastener insertion axis. The system also includes a fastener that includes an elongate portion and a head portion. The elongate portion extends along an insertion axis defined by the pivot member bore and the head portion is engaged with the pivot member to radially expand the pivot member to frictionally engage the sidewall with the outer surface to restrict displacement of the nut within the aperture relative to the plate body.

A number of feature refinements and additional features are applicable to the second aspect. These feature refinements and additional features may be used individually or in any combination. As such, each of the following features that will be discussed may be, but are not required to be, used with any other feature or combination of features of the second aspect. Moreover, any of the foregoing features or feature refinements described in relation to the first aspect may be utilized in any combination with the second aspect.

In an embodiment of the second aspect, the elongate portion of the fastener may engage the bone of a patent to compressingly engage the head portion relative to the pivot member to expand the pivot member radially relative to the insertion axis. As may be appreciated, this may be provided as an alternative to the threaded engagement described above in which the fastener is loaded without compression forces acting thereon.

A third aspect includes a method of use of an orthopedic system. The method includes placing a plate body that extends between an upper surface and a lower surface relative to a bone of a patient such that the lower surface is in contacting engagement with the bone of the patient. The plate body includes an aperture extending through the plate body from the upper surface to the lower surface along a reference axis and includes a pivot member retained within the aperture that defines a bore extending along a fastener insertion axis. The method includes articulating the pivot member relative to the plate body to define an included angle between the reference axis and the fastener insertion axis. The method also includes disposing an elongate portion of a fastener through the bore of the pivot member such that the fastener is advanced along the insertion axis and advancing the fastener relative to the pivot member such that a head portion of the fastener engages the pivot member. The method further includes expanding the pivot member radially relative to the fastener insertion axis in response to the advancing such that the pivot member frictionally engages the aperture to restrict articulation of the pivot member relative to the plate body.

A number of feature refinements and additional features are applicable to the third aspect. These feature refinements and additional features may be used individually or in any combination. As such, each of the following features that will be discussed may be, but are not required to be, used with any other feature or combination of features of the third aspect. Moreover, any of the foregoing features or feature refinements described in relation to the first or second aspects may be utilized in any combination with the third aspect.

For instance, the pivot member may include an expansion slot and the expanding may include expanding the nut relative to the expansion slot. The expanding may also include contacting a sidewall of the aperture with an outer surface of the pivot member.

In addition, the advancing may also include engaging threads on the head portion of the fastener with corresponding threads disposed on the bore of the pivot member. In turn, the method may include locking the head portion of the fastener to the pivot member in response to the engaging of the threads on the heads with the threads disposed on the bore of the pivot member.

In an embodiment, the articulating may include movement of the pivot member in the aperture relative to the plate body in at least one degree of freedom. The articulating may include movement of the pivot member in the aperture relative to the plate body in at least two degrees of freedom. The articulating may include movement of the pivot member in the aperture relative to the plate body such that the included angle is definable at any radial position about the reference axis. The included angle between the reference axis and the insertion axis may be at least about 10 degrees. The included angle between the reference axis and the insertion axis may be at least about 15 degrees.

A fourth aspect includes an orthopedic fastener assembly for use in fixation of an orthopedic plate to a bone of a patient. The assembly includes a fastener that includes an elongate portion and a head portion. The elongate portion is on a distal portion of the fastener and includes threads for engagement with a bone of a patient. The head portion is disposed at a proximate portion of the fastener. The assembly also includes a pivot member that includes a bore having a contoured surface disposed about and pivotally displaceable relative to the head portion for pivotal articulation of the pivot member about the head portion. The pivot member is moveable relative to the head portion and secured thereto to prevent removal of the pivot member from the head portion.

A number of feature refinements and additional features are applicable to the fourth aspect. These feature refinements and additional features may be used individually or in any combination. As such, each of the following features that will be discussed may be, but are not required to be, used with any other feature or combination of features of the fourth aspect. Moreover, any of the foregoing features or feature refinements described in relation to the first through third aspects may be utilized in any combination with the fourth aspect.

For instance, the bore may define a reference axis and the fastener may extend along a fastener insertion axis. In turn, the pivotal articulation of the pivot member about the head portion may define an included angle between the reference axis and the fastener axis. The included angle between the reference axis and the fastener insertion axis may be definable at any radial position about the reference axis. The included angle may be at least about 10 degrees. The included angle may alternatively be at least about 15 degrees.

In various embodiments, the pivot member may include engagement features to lockingly engage the pivot member to a plate through which the fastener has been advanced. For instance, in an embodiment, the contoured surface and the head portion may be non-circular and interface to restrict rotation of the pivot member about a fastener insertion axis extending along the elongate portion. In turn, the pivot member comprises a first locking feature that correspond to and are engageable with a second locking feature on a plate through which the fastener is advanceable. The first locking feature may include a ramped surface engageable with corresponding teeth on a plate through which the fastener is advanceable to allow for rotation of the pivot member in a first direction relative to the plate and to restrict rotation in a second direction opposite the first direction when the ramped surface engages the corresponding teeth on the plate. The contoured surface may be circumferentially arcuate about the bore and the pivot member is rotatable about the head portion about the fastener insertion axis.

In an alternative embodiment, the first locking feature may include a ramped surface engageable with a corresponding shoulder on a sidewall of an aperture extending through a plate through which the fastener is advanceable. The ramped surface may be rotationally displaceable relative to the shoulder to lockingly engage the pivot member relative to the plate. The bore of the pivot member may further include a sloped surface extending away from the locking axis in a proximal direction. In turn, coordinated engagement of the ramped surface and the shoulder may urge the pivot member proximally to lockingly engage the pivot member relative to the plate in response to rotation of the pivot member in a first rotational direction. In addition, the shoulder may include a lip for coordinated engagement of a trailing edge of the ramped surface to restrict rotation of the pivot member in a second rotational direction opposite the first rotational direction.

A fifth aspect includes an orthopedic system for use in fixation of an orthopedic plate to a bone of a patient. The system includes a fastener comprising an elongate portion on a distal portion of the fastener. The elongate portion includes threads for engagement with a bone of a patient and a head portion at a proximate portion of the fastener. The fastener extends along a fastener insertion axis. The system also includes a pivot member comprising a bore that defines a locking axis. The bore includes a contoured surface disposed about and pivotally displaceable relative to the head portion for non-removable engagement therewith. The contoured surface is moveable relative to the head portion for articulation of the pivot member relative to the head portion to define an included angle between the locking axis and the fastener insertion axis. The pivot member comprises a first locking feature. The system also includes a plate extending between an upper surface and a lower surface and having an aperture extending through the plate from the upper surface to the lower surface along a reference axis. The aperture comprises a second locking feature. In turn, the locking axis is alignable with the reference axis as the fastener is advanced relative to the plate along the fastener insertion axis and the first and second locking features are engageable upon rotational of the pivot member relative to the plate to engage the pivot member with the plate to prevent rotational retraction of the pivot member. When engaged with the plate, the pivot member maintains the included angle between the fastener insertion axis and the locking axis.

A number of feature refinements and additional features are applicable to the fifth aspect. These feature refinements and additional features may be used individually or in any combination. As such, each of the following features that will be discussed may be, but are not required to be, used with any other feature or combination of features of the fifth aspect. Moreover, any of the foregoing features or feature refinements described in relation to the first through fourth aspects may be utilized in any combination with the fifth aspect.

For instance, in an embodiment, the included angle between the locking axis and the fastener insertion axis may be definable at any radial position about the reference axis. The included angle may be at least about 10 degrees. Alternatively, the included angle is at least about 15 degrees.

In an embodiment, the contoured surface and the head portion may be non-circular and may interface to restrict rotation of the pivot member about a fastener insertion axis extending along the elongate portion. In turn, the pivot member may include a first locking feature that correspond to and are engageable with a second locking feature on the plate. The first locking feature may include a ramped surface engageable with corresponding teeth on the plate to allow for rotation of the pivot member in a first direction relative to the plate and to restrict rotation in a second direction opposite the first direction when the ramped surface engages the corresponding teeth on the plate.

In an alternative embodiment, the contoured surface may be circumferentially arcuate about the bore and the pivot member is rotatable about the head portion about the fastener insertion axis. The pivot member may include a first locking feature that may correspond to and are engageable with a second locking feature on the plate. The first locking feature may include a ramped surface engageable with a corresponding shoulder on the sidewall of the aperture. The ramped surface may be rotationally displaceable relative to the shoulder to lockingly engage the pivot member relative to the plate. The bore of the pivot member may include a sloped surface extending away from the locking axis in a proximal direction. In turn, coordinated engagement of the ramped surface and the shoulder may urge the pivot member proximally to lockingly engage the pivot member relative to the plate in response to rotation of the pivot member in a first rotational direction. The shoulder may include a lip for coordinated engagement of a trailing edge of the ramped surface to restrict rotation of the pivot member in a second rotational direction opposite the first rotational direction.

A sixth aspect includes a method of use of an orthopedic system. The method includes placing a plate body that extends between an upper surface and a lower surface relative to a bone of a patient such that the lower surface is in contacting engagement with the bone of the patient. The plate body comprises an aperture extending through the plate body from the upper surface to the lower surface along a reference axis. The method also includes advancing a fastener relative to the aperture along a fastener insertion axis. The reference axis and the fastener insertion axis define an included angle therebetween. The method also includes disposing a pivot member that is disposed about and pivotally displaceable relative to a head portion of the fastener for non-removable engagement therewith within the aperture in response to the advancing. The method also includes engaging a first locking feature on the pivot member with second locking features of the aperture to lockingly engage the fastener relative to the plate.

A number of feature refinements and additional features are applicable to the sixth aspect. These feature refinements and additional features may be used individually or in any combination. As such, each of the following features that will be discussed may be, but are not required to be, used with any other feature or combination of features of the sixth aspect. Moreover, any of the foregoing features or feature refinements described in relation to the first through fifth aspects may be utilized in any combination with the sixth aspect.

For instance, the engaging may include rotating the pivot member in response to rotational advancement of the fastener. The engaging may further include contacting the first locking feature comprising a ramped surface with corresponding teeth on the plate to allow for rotation of the pivot member in a first direction relative to the plate and restricting rotation in a second direction opposite the first direction in response to the engaging.

Alternatively the engaging may include rotation of the pivot member independently of the fastener member. In turn, the engaging may include engaging the first locking feature that comprises a ramped surface with a corresponding shoulder on the sidewall of the aperture in response to the rotation of the pivot member. The bore of the pivot member may include a sloped surface extending away from the locking axis in a proximal direction. In turn, the method may include engaging the ramped surface and the shoulder urges the pivot member proximally to lockingly engage the pivot member relative to the plate in response to rotating the pivot member in a first rotational direction. A such, the method may include restricting rotation of the pivot member in a second rotational direction opposite the first rotational direction with a lip on the shoulder for coordinated engagement of a trailing edge of the ramped surface.

A seventh aspect include an orthopedic fastener assembly that facilitates variable angulation of the orthopedic fastener assembly when used for fixation of a plate to a bone. The assembly includes a fastener that includes an elongate portion, a ledge, and a head portion. The elongate portion is disposed at a distal portion of the fastener and includes threads for engagement with a bone of a patient and extending along a fastener insertion axis. The ledge extends from the elongate portion radially relative to the fastener insertion axis. The head portion is disposed at a proximate portion of the fastener. The head portion is selectively displaceable relative to the elongate portion. The assembly also includes a pivot member that includes an expansion slot that allows for radial expansion of the pivot member radially relative to the fastener insertion axis and a bore that defines a locking axis. The pivot member is disposed between the head portion and the ledge such that the pivot member extends about the elongate portion. As such, the head portion is distally advanceable relative to the pivot member to contact the pivot member with a ramp surface of the head portion to radially expand the pivot member upon the distal advancement of the head portion relative to the elongate portion.

A number of feature refinements and additional features are applicable to the seventh aspect. These feature refinements and additional features may be used individually or in any combination. As such, each of the following features that will be discussed may be, but are not required to be, used with any other feature or combination of features of the seventh aspect. Moreover, any of the foregoing features or feature refinements described in relation to the first through sixth aspects may be utilized in any combination with the seventh aspect.

For instance, the head portion may be threadably engaged with a proximal portion of the elongate portion. This may facilitate relative movement between the head portion and the elongate portion. As such, the head portion may be distally or proximally displaced relative to the elongate portion in response to rotation of the head portion relative to the elongate portion.

In an embodiment, the proximal portion may include a first tool receiving portion and the head portion may include a second tool receiving portion. The first tool receiving portion may be engageable for controllable rotation of the elongate member. As such, a first tool engaged with the first tool receiving portion may be used to rotatably advance the elongate portion relative to a bone of the patient.

The second tool receiving portion may be engageable for controllable rotation of the head portion. As such, a second tool may be engageable with the second tool receiving portion to rotate the head portion for advancement or retraction of the head portion relative to the elongate portion.

The pivot member may include an outer surface adapted for frictional engagement with a sidewall of an aperture in a plate through which the fastener is advanceable upon radial expansion of the pivot member. The aperture in the plate through which the fastener is advanceable may define a reference axis and the fastener insertion axis may be displaceable relative to the reference axis to define an included angle. The included angle between the reference axis and the fastener insertion axis may be definable in at least one degree of freedom. The included angle between the reference axis and the fastener insertion axis may be definable in at least two degrees of freedom. Moreover, the included angle between the reference axis and the fastener insertion axis may be definable at any radial position about the reference axis. The included angle between the reference axis and the insertion axis is at least about 15 degrees.

An eighth aspect includes an orthopedic system for fixation of an orthopedic plate to a bone of a patient. The system includes a plate body extending between an upper surface and a lower surface of the plate body. The system includes an aperture extending through the plate body from the upper surface to the lower surface along a reference axis. The aperture has a sidewall extending circumferentially about an interior of the aperture. The system also includes a fastener that includes an elongate portion at a distal portion of the fastener comprising threads for engagement with a bone of a patient and extending along a fastener insertion axis. A ledge extends from the elongate portion radially relative to the fastener insertion axis. Further still, a head portion is provided at a proximate portion of the fastener. The head portion is selectively displaceable relative to the elongate portion. The system includes a pivot member having an outer surface corresponding to the sidewall and comprising an expansion slot that allows for radial expansion of the pivot member radially relative to the fastener insertion axis and a bore that defines a locking axis. The pivot member is disposed between the head portion and the ledge such that the pivot member extends about the elongate portion. In turn, the fastener is advanceable relative to the aperture to dispose the pivot member relative to the sidewall and the head portion is distally advanceable relative to the pivot member to contact the pivot member with a ramp surface of the head portion to radially expand the pivot member upon the distal advancement of the head portion relative to the elongate portion to frictionally engage the sidewall with the outer surface to lockingly engage the fastener relative to the plate.

A number of feature refinements and additional features are applicable to the eighth aspect. These feature refinements and additional features may be used individually or in any combination. As such, each of the following features that will be discussed may be, but are not required to be, used with any other feature or combination of features of the eighth aspect. Moreover, any of the foregoing features or feature refinements described in relation to the first through seventh aspects may be utilized in any combination with the eighth aspect.

For instance, in an embodiment, the aperture may include a neck portion with a diameter less than the pivot member. In turn, the pivot member may radially constrict when advanced relative to the neck portion of the aperture. The aperture may include a pocket distal to the neck portion comprising the sidewall. As such, the pivot member may be disposed in the pocket upon advancement of the fastener relative to the plate.

A ninth aspect includes a method of use of an orthopedic system. The method includes placing a plate body that extends between an upper surface and a lower surface relative to a bone of a patient such that the lower surface is in contacting engagement with the bone of the patient. The plate body comprises an aperture extending through the plate body from the upper surface to the lower surface along a reference axis. The method further includes advancing a fastener relative to the aperture along a fastener insertion axis. The reference axis and the fastener insertion axis define an included angle therebetween. The method also includes disposing a pivot member that is disposed between a head portion and a ledge of the fastener for non-removable engagement therewith within the aperture in response to the advancing. The method includes moving the head portion relative to the ledge and contacting a ramped surface of the head portion with the pivot member. The method also includes radially expanding the pivot member in response to the contacting and frictionally engaging a sidewall of the aperture with an outer surface of the pivot member in response to the radially expanding to lockingly engage the fastener to the plate.

A number of feature refinements and additional features are applicable to the ninth aspect. These feature refinements and additional features may be used individually or in any combination. As such, each of the following features that will be discussed may be, but are not required to be, used with any other feature or combination of features of the ninth aspect. Moreover, any of the foregoing features or feature refinements described in relation to the first through eighth aspects may be utilized in any combination with the ninth aspect.

DETAILED DESCRIPTION

Figure 1:
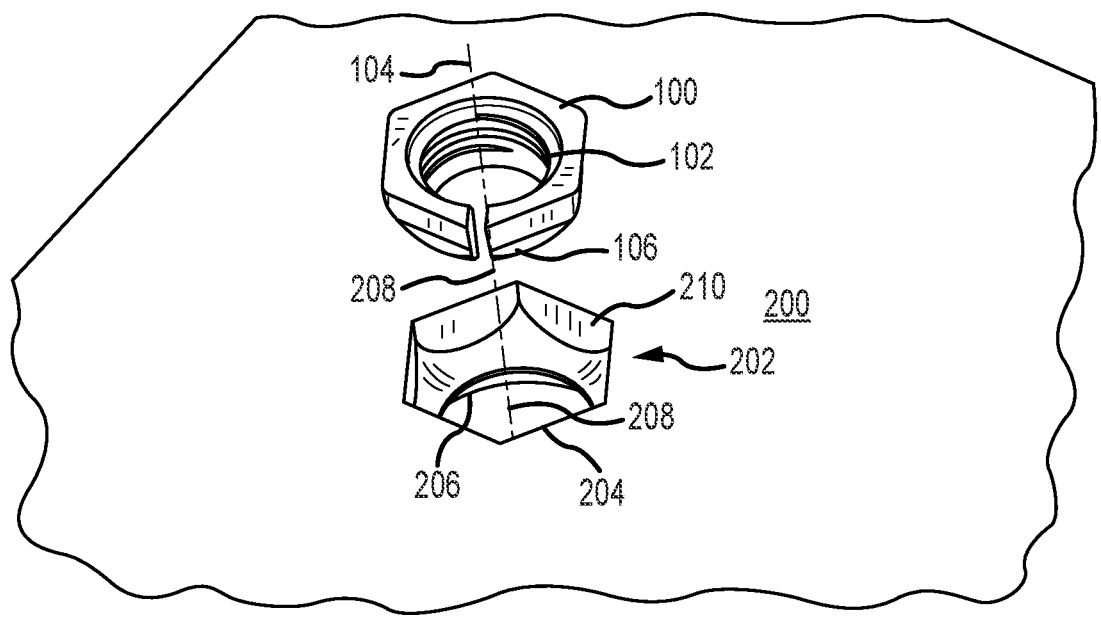
FIG. 1 is a perspective view of an embodiment of a pivot member and an orthopedic plate in an exploded state.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

FIG. 1 depicts an embodiment of a pivot member 100 and a plate 200. The plate 200 may include an aperture 202 extending between an upper surface 204 of the plate 200 and a lower surface 206 of the plate. The aperture 202 may be sized so as to receivingly engage the pivot member 100, which is shown in an exploded state in FIG. 1. The aperture 202 may extend along and define a reference axis 208.

Figure 2:
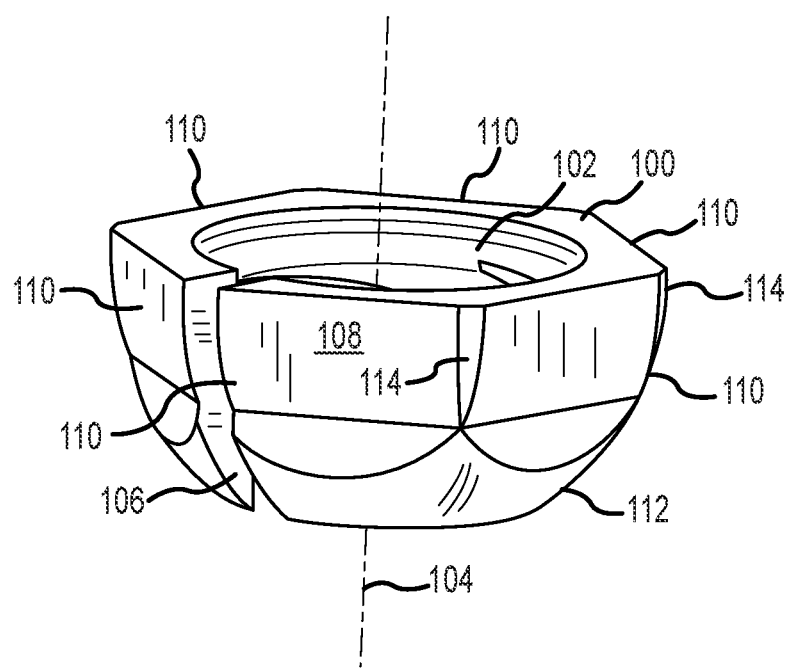
FIG. 2 is a perspective view of an embodiment of a pivot member.

With additional reference to FIG. 2, the pivot member 100 may include a bore 102. The bore 102 may, in at least some embodiments, be threaded. In any regard, the bore 102 may define a fastener insertion axis 104 along which a fastener (not shown in FIGS. 1 and 2) may be advanced relative to the pivot member 100.

The pivot member 100 may comprise an expansion slot 106. The expansion slot 106 may define a gap or opening of the pivot member 100 that extends along the entire pivot member 100 in a direction corresponding to (e.g., parallel with) the fastener insertion axis 104. Alternatively, the expansion slot 106 may not extend along the entire distance of the pivot member 100. For instance, the expansion slot 106 may only extend along a portion of the distance of the pivot member 100 in a direction corresponding to the fastener insertion axis 104. Moreover, in an embodiment that the expansion slot 106 does not extend entirely along the distance of the pivot member 100, a plurality of expansion slots 106 may be provided radially about the pivot member 100. In any regard, the expansion slot 106 may facilitated radial expansion of the pivot member 100 relative to the fastener insertion axis 104.

Figure 4:
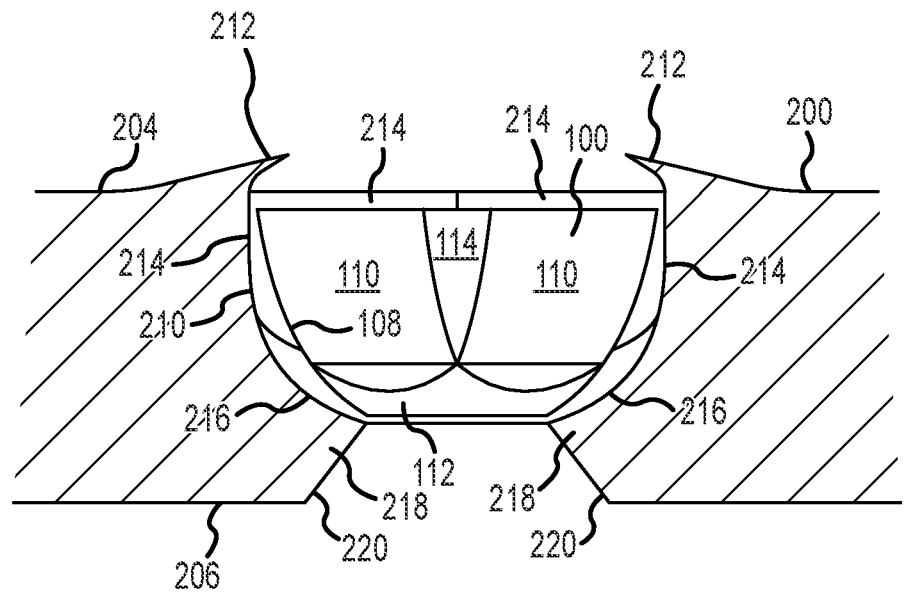
FIG. 4 is a partial cross sectional view of an embodiment of a pivot member in retained engagement with a plate.
Figure 5:
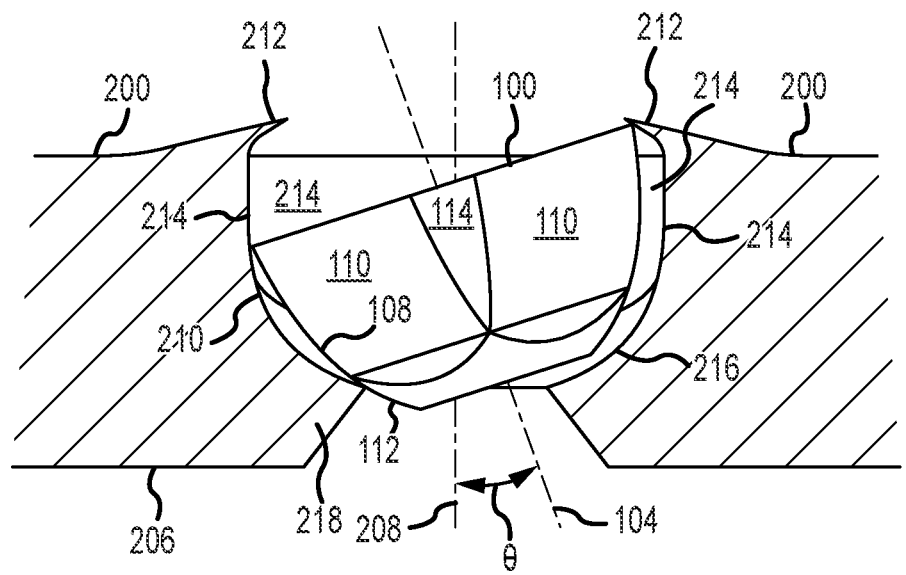
FIG. 5 is a partial cross sectional view of an embodiment of a pivot member in retained engagement with a plate in a pivoted position.

In addition, the pivot member 100 may comprise an outer surface 108 that is of a shape corresponding to a sidewall 210 of the aperture 202. The sidewall 210 may extend circumferentially about the aperture 202. In this regard, can be seen in FIG. 3, the pivot member 100 may be alignable with and received in the aperture 202. When the aperture 202 receives the pivot member 102, the outer surface 108 of the pivot member 100 may be in conformal adjacent relation to the sidewall 210 of the aperture 202. For instance, as shown in FIG. 4, the pivot member 100 may be received in the aperture 202 such that the outer surface 108 of the pivot member 100 is disposed in adjacent relation to the sidewall 210 of the aperture 202. With further reference to FIG. 5, the conformal corresponding outer surface 108 and sidewall 210 may allow for pivotal movement of the pivot member 100 relative to the aperture 202. In turn, the fastener insertion axis 104 and the reference axis 208 may be disposed to define an included angle θ therebetween.

As may be appreciated, the pivot member 100 may be capable of pivotal movement relative to the plate 200 in at least one degree of freedom to define the included angle θ. In a preferred embodiment, the pivot member 100 may be capable of pivotal movement relative to the plate 200 in at least two degrees of freedom. In this regard, the included angle θ may be defined at any radial position about the reference axis 208. That is, if considering the possible positions of the fastener insertion axis 104 relative to the reference axis 208 as defining a field of possible positions, the fastener insertion axis 104 may be disposed in any position defining a cone extending along the reference axis 208. In addition, the plate 200 may comprise a skirted portion 220 that may facilitate acceptance of a fastener within the bore 102 when the pivot member 100 is disposed at the included angle θ. In this regard, the pivot member 100 may be pivotal relative to the plate 200 such that the included angle θ is at least 10 degrees. In alternate embodiments, the included angle θ may be at least about 15 degrees.

Figure 3:
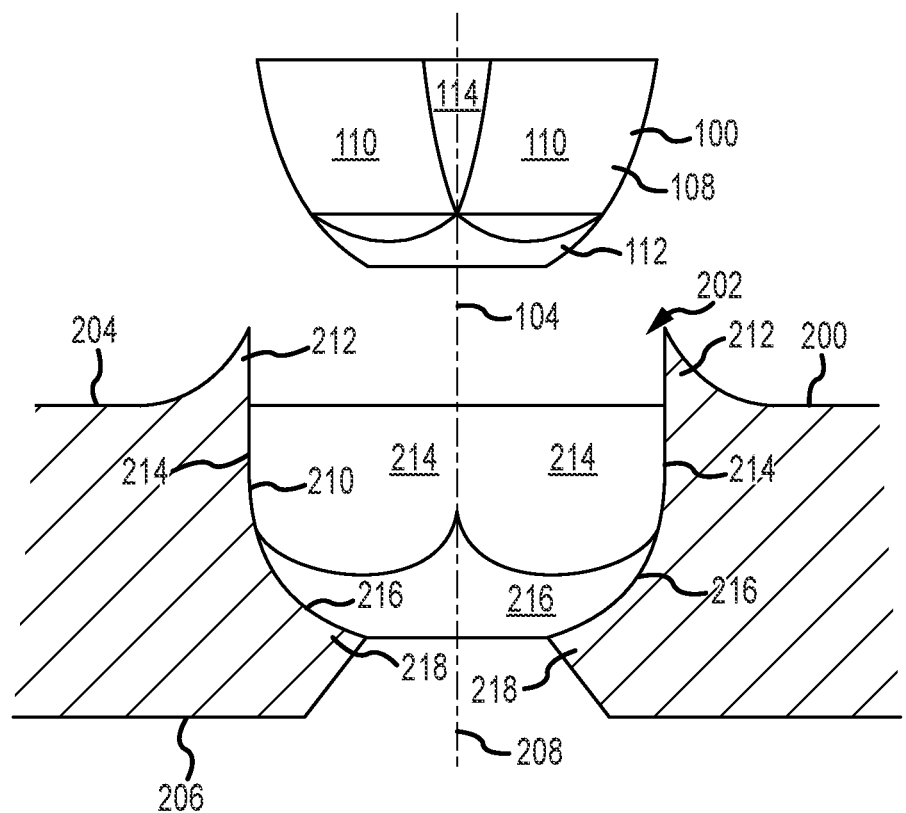
FIG. 3 is a partial cross sectional view of an embodiment of a pivot member in an exploded position relative to an aperture of a plate.

With returned reference to FIG. 3, prior to insertion of the pivot member 100 into the aperture 202, an extension 212 may extend from the upper surface 204 adjacent to the aperture 202. As shown in a first configuration in FIG. 3, the extension 212 may be disposed to allow for the pivot member 100 to be received in the aperture 202. Upon receipt of the pivot member 100 in the aperture 202, the extension 212 may be displaced toward the reference axis 208 as shown in FIGS. 4 and 5. As can be seen in particular in FIG. 5, the extension 212, when displaced after the pivot member 100 is received in the aperture 202 may assist in retaining the pivot member 100 within the aperture 202. That is, when the pivot member 100 is pivoted relative to the aperture 202, the extension 212 may comprise a portion of the conformal, adjacent sidewall 210 of the aperture 202 to retain the pivot member 100 within the aperture.

Figure 29:
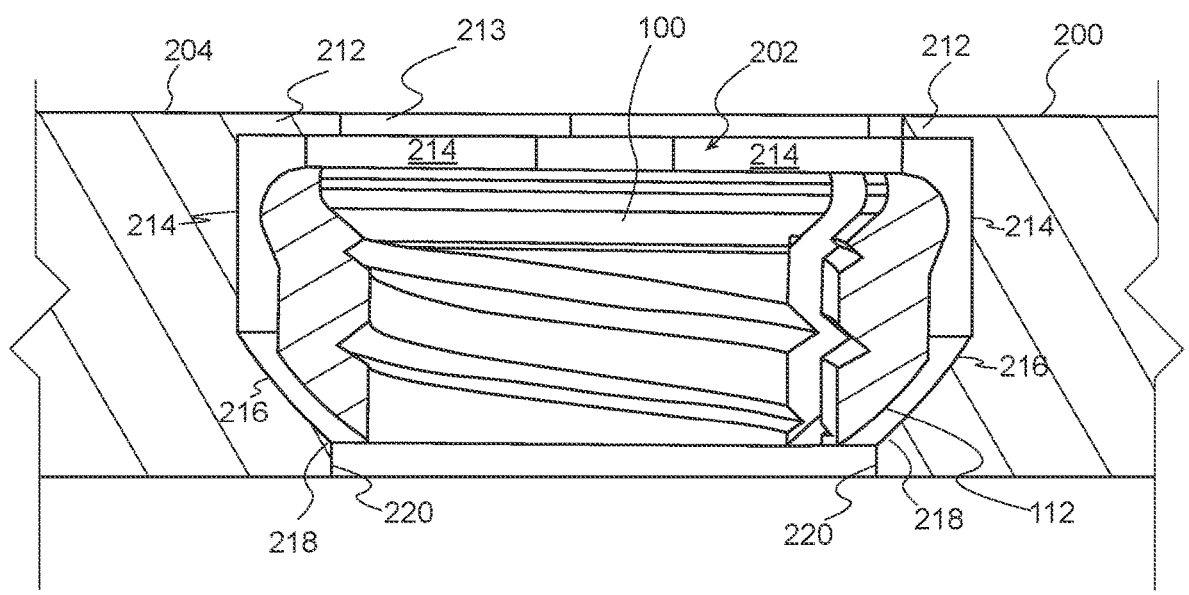
FIG. 29 is an alternate embodiment of a pivot member in retained engagement with a plate.

FIG. 29 depicts an alternate embodiment of a plate 200 having an extension 212 that extends parallel to the upper surface 204. In this regard, the extensions 212 may define a hole 213 that has a smaller cross dimension than the aperture 202. In this regard, the pivot member 100 may be retracted or collapsed to allow for passage through the hole 213. Once disposed in the aperture 202, the pivot member 100 may be expanded such that the extension member 212 extending parallel to the upper surface 204 may restrict the pivot member 100 from being removed from the aperture 202.

In this regard, the pivot member 100 may be disposed in and retained by the aperture 202. This arrangement may be established prior to the use of the plate 200 in a surgical operation. Because the pivot member 100 is retained within the aperture 202, a surgeon or other user during surgery may not be required to manipulate the pivot member 100 to dispose it relative to a fastener and/or the plate 200. In turn, the plate 200 may be provided as a unitary component to the surgeon for use in affixing the plate 200 to a bone of a patient without having the added complexity of alignment and engagement of the pivot member 100 relative to the plate 200.

Figure 6:
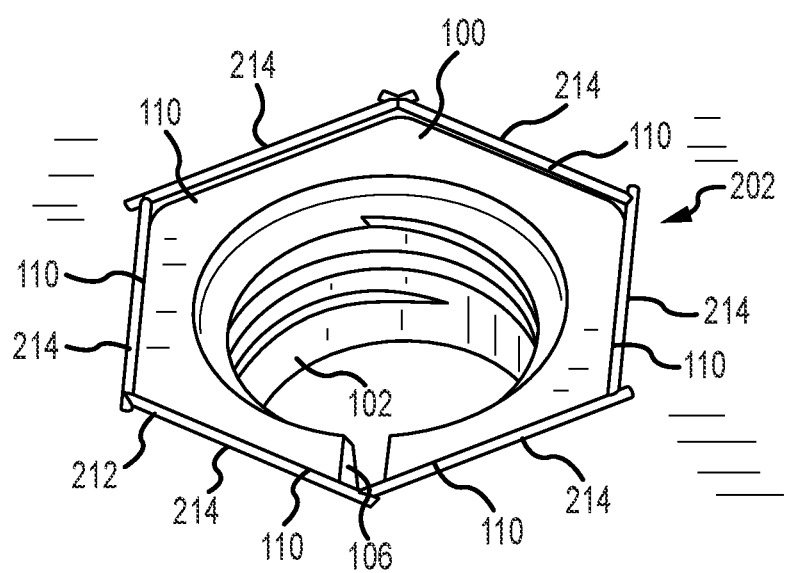
FIG. 6 is a perspective view of an embodiment of a pivot member in retained engagement in a plate.

In an embodiment, the outer surface 108 of the pivot member 100 may be noncircular. In corresponding relation, the sidewall 210 of the aperture 202 may also have at least a portion that is non-circular. In this regard, the outer surface 108 and the sidewall 210 may interface to restrict rotation of the pivot member 100 relative to the aperture 202. For instance, the pivot member 100 may comprise a plurality of flats 110 that correspond to flat portions 214 of the aperture 202 as can be seen in FIG. 6. Chamfers 114 may be provided between the flats 110 as can best be seen in FIGS. 2-5. The chamfers 114 may assist in facilitating pivoting of the pivot member 110 relative to the aperture 202 (e.g., to provide two degrees of freedom of movement of the pivot member 100 relative to the plate 200 as described above).

In addition, the pivot member 100 may include a convex portion 112. The convex portion 112 may be in conformal adjacent relation to a ramped surface 216. The ramped surface 216 may extend along a flange 218 that extends from the sidewall 210 toward the reference axis 208. In this regard, the flange 218 and ramped surface 216 may comprise a bowled portion that receives the convex portion 112 of the pivot member 110 when the pivot member 100 is disposed in the aperture 202.

Figure 7:
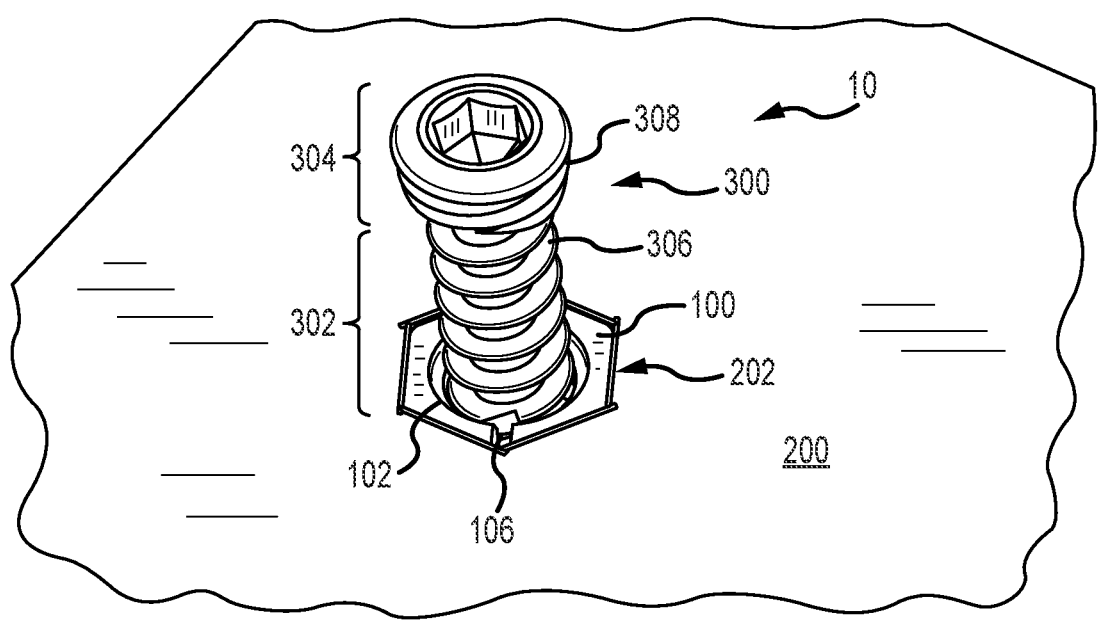
FIG. 7 is a perspective view of an embodiment of an orthopedic implant system comprising a pivot member in retained engagement with a plate in which a fastener is threadably engaged with the pivot member.
Figure 8:
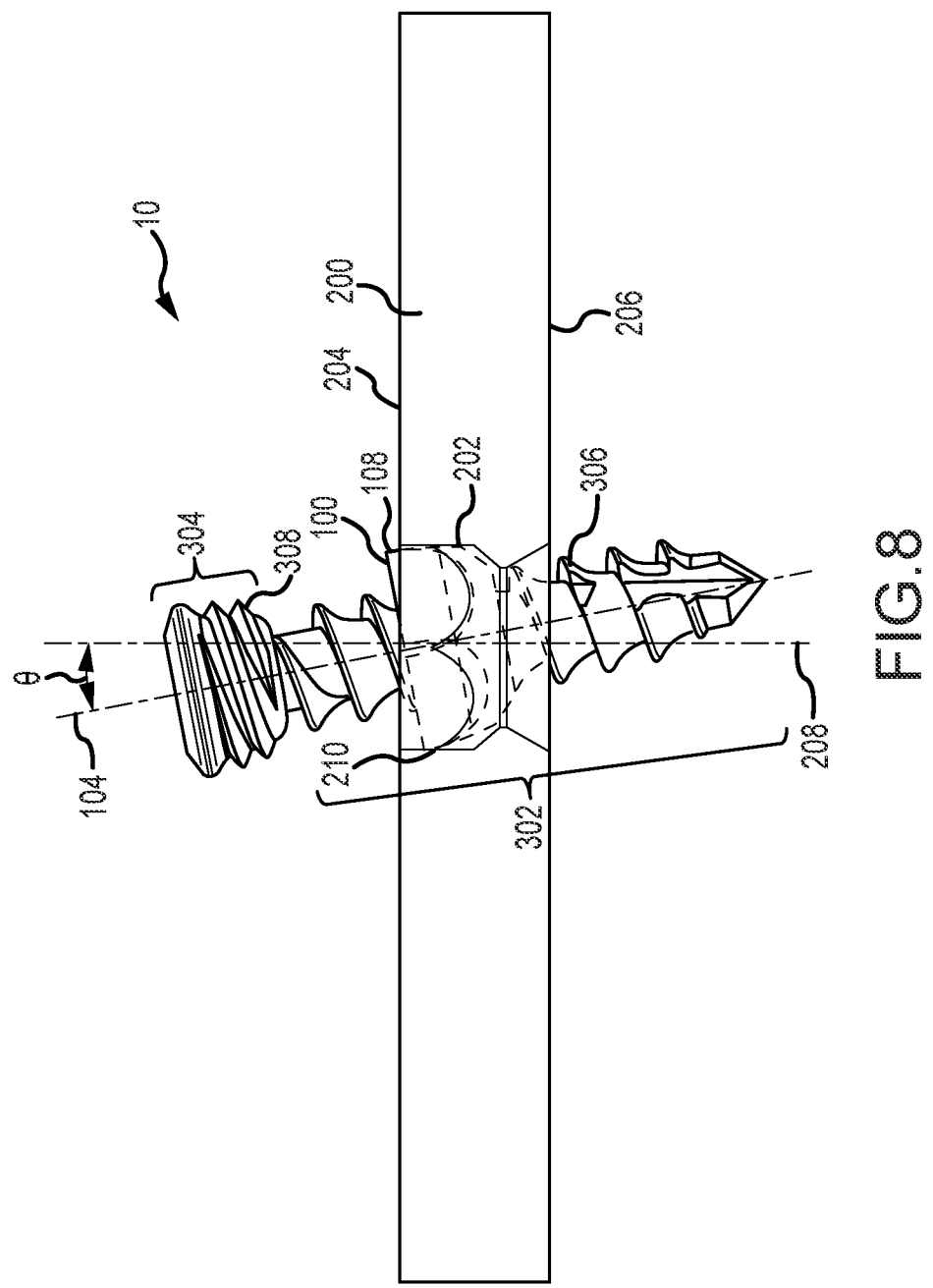
FIG. 8 is a partial cross sectional view of the embodiment of the orthopedic implant system as shown in FIG. 7.

With further reference to FIG. 7, an embodiment of a fastener 300 is shown relative to the pivot member 100 and plate 200. The pivot member 100, plate 200, and fastener 300 may comprise an orthopedic implant system 10. The fastener 300 may comprise a screw such as a surgical screw or the like. The fastener 300 may comprise a self-tapping screw, or include any other features common to surgical screws. The fastener 300 may comprise an elongate portion 302 at a distal portion of the fastener 300 and a head portion 304 at a proximal portion of the fastener 300. The elongate portion 302 may comprise threads 306. In this regard, the fastener 300 may be in threaded engagement with corresponding threads disposed about the bore 102 of the pivot member 100. In addition, the threads 306 of the fastener 300 may be used to advance the fastener 300 relative to a bone of a patient for securing the fastener 300 to the bone after having passed through the pivot member 100 and plate 200.

The head portion 304 may also comprise threads 308. The threads 308 may be the same pitch as the threads 306 of the elongate portion 302. In addition, the threads 308 on the head portion 304 may comprise a double thread. In this regard, two threads of the same pitch may be provided on the head portion 304. In this regard, the pitch of the threads 306 of the elongate portion 302 may be the same as the pitch of the threads 308 of the head portion 304 with the head portion 304 featuring a double thread. Both threads 306 and 308 may engage with the threads of the bore 102, or threads 308 on the head portion 304 alone may engage the threads of the bore 102. In this latter regard, the threads 306 on the elongate portion 302 may be provided to engage the bone of a patient, yet may not contact the pivot member 100 as the fastener 300 is advanced relative thereto. The head portion 304 may have a sloped surface that defines a profile such that the diameter of the head increases toward the proximal end of the fastener 300. For instance, the head portion 304 may be frustoconical. In any regard, the pitch diameter of the fastener 300 may increase toward the proximal end of the fastener 300.

In turn, the interaction of the fastener 300 may result in locking of the pivot member 100 relative to the plate 200. Specifically, as described above, the pivot member 100 may be expandable radially in relation to the fastener insertion axis 104. For instance, the interaction of the fastener 300 (e.g., the head portion 304 thereof) as it is advanced relative to the pivot member 100 may cause the radial expansion of the pivot member 100. In turn, the outer surface 108 of the pivot member 100 may frictionally engage the sidewall 212 of the aperture 202. The frictional engagement of the outer surface 108 with the sidewall 210 may at least limit, and in some instances prevent, movement of the pivot member 100 relative to the plate 200.

Figure 9:
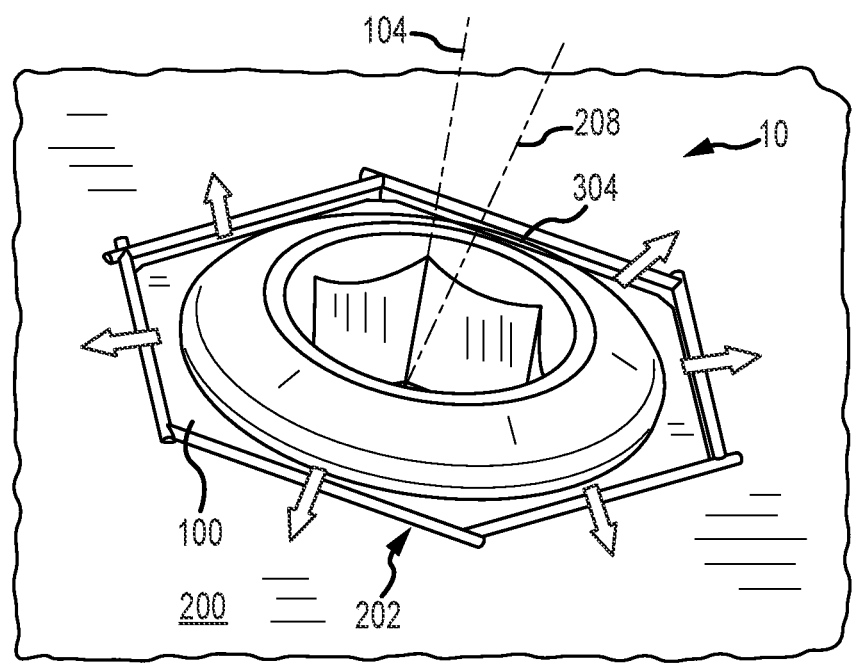
FIG. 9 is a perspective view of an embodiment of an orthopedic implant system in which a fastener is in a fully advanced position relative to a pivot member and a plate.
Figure 10:
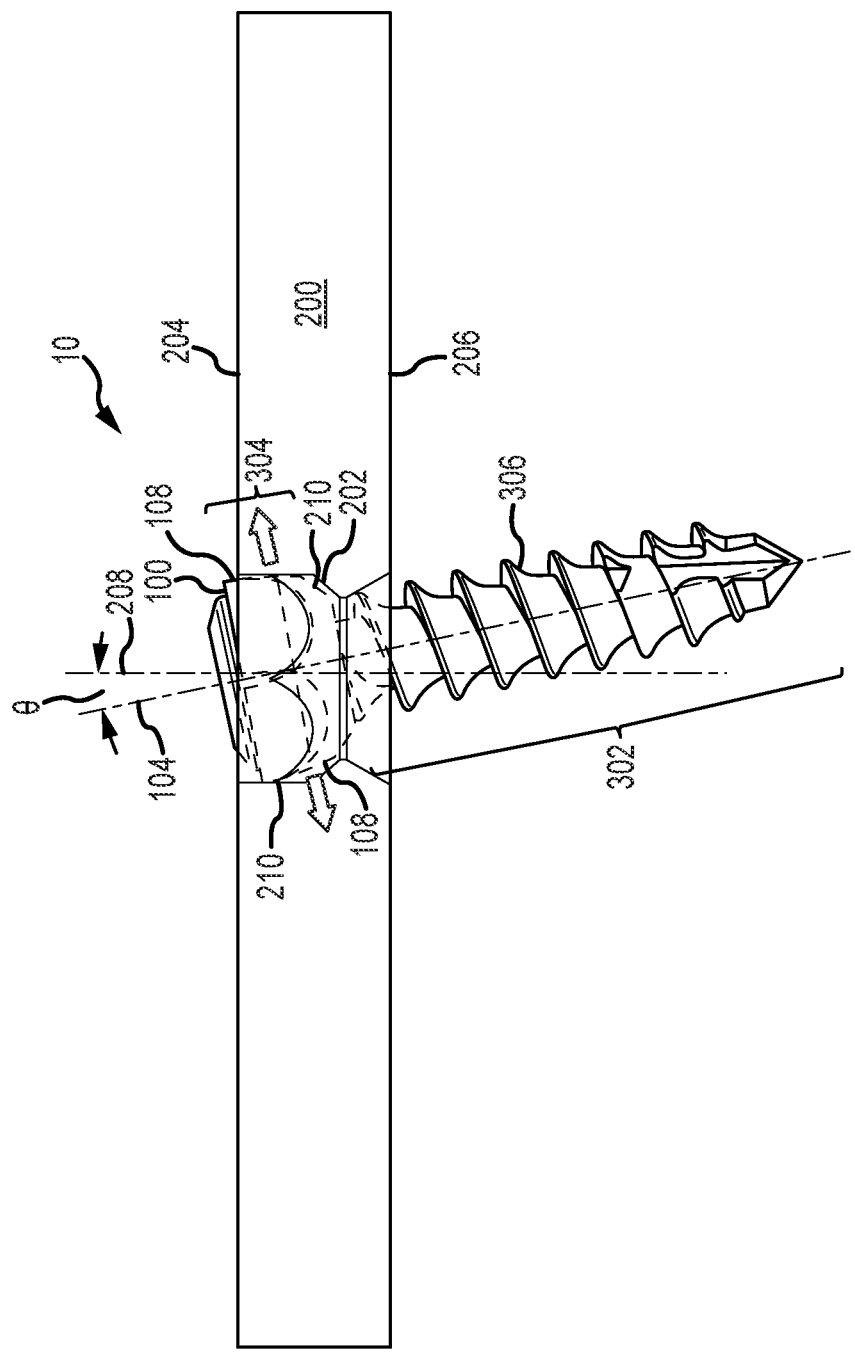
FIG. 10 is a partial cross sectional view of the embodiment of the orthopedic implant system as shown in FIG. 9.

In some embodiments, the threaded engagement of the threads 308 of the head portion 304 of the fastener 300 may act on the bore 102 to radially expand the pivot member 100 relative to the aperture 202 to from a first configuration as shown in FIG. 6 to a second configuration as shown in FIGS. 9 and 10. In the first configuration, the outer surface 108 may be moveable relative to the conformal adjacent sidewall 210 of the aperture 202. However, in the second configuration, the outer surface 108 of the pivot member 100 may contactingly engage the sidewall 210.

Upon advancement of the fastener 300 relative to the pivot member 100, the head portion 304 may threadingly engage the bore 102 of the pivot member 100. As the head portion 304 may have an increased diameter as compared to the elongate portion 302 (e.g., including potentially including a frustoconically shaped portion with increasing diameter along the head portion 304 in a proximal direction), the engagement of the head portion 304 with the pivot member 100 may expand the pivot member 100 radially relative to the fastener insertion axis 104 to the second configuration as shown in FIGS. 9 and 10. That is, the second configuration of the pivot member 100 may be at a greater radial expansion than that of the first configuration.

In the second configuration, the outer surface 108 of the pivot member 100 may engage the sidewall 210 of the aperture 202 to restrict movement of the pivot member 100 relative to the plate 200. In this second configuration, the movement of the pivot member 100 relative to the plate 200 may be fully restricted such that forces imparted by a surgeon, forces resulting from installation of the plate 200 to the bone of a patient, or forces that are imparted to the pivot member 100, plate 200, and fastener 300 once installed do not result in movement of the pivot member 100 relative to the plate 200. In an embodiment, the head portion 304 threadably engages the bore 102 when the head portion 304 is advanced to the pivot member 100. In this regard, the fastener 300 may be rigidly engaged with the pivot member 100 that is in turn frictionally engaged with the aperture 202.

In other embodiments, the conical or frustoconical shape of a head portion 304 without threads may also be used. In this embodiment, the advancement of the fastener 300 relative to the bone of a patient may cause compressive forces to act on the pivot member 100 such that the frustoconical head portion 304 still results in radial expansion of the pivot member 100 to frictionally engage the aperture 202 as illustrated in FIG. 9. Accordingly, the fastener 300 may be lockingly engageable with the pivot member 100 by threaded interaction therebetween such that the fastener 300 is in turn loaded without compression forces acting between the fastener 300 and the plate 200. In contrast, the fastener 300 may lacking locking threads to lock the fastener 300 to the pivot member 100 such that the fastener 300 may be loaded in compression to lock the pivot member 100 relative to the plate 200.

Figure 11:
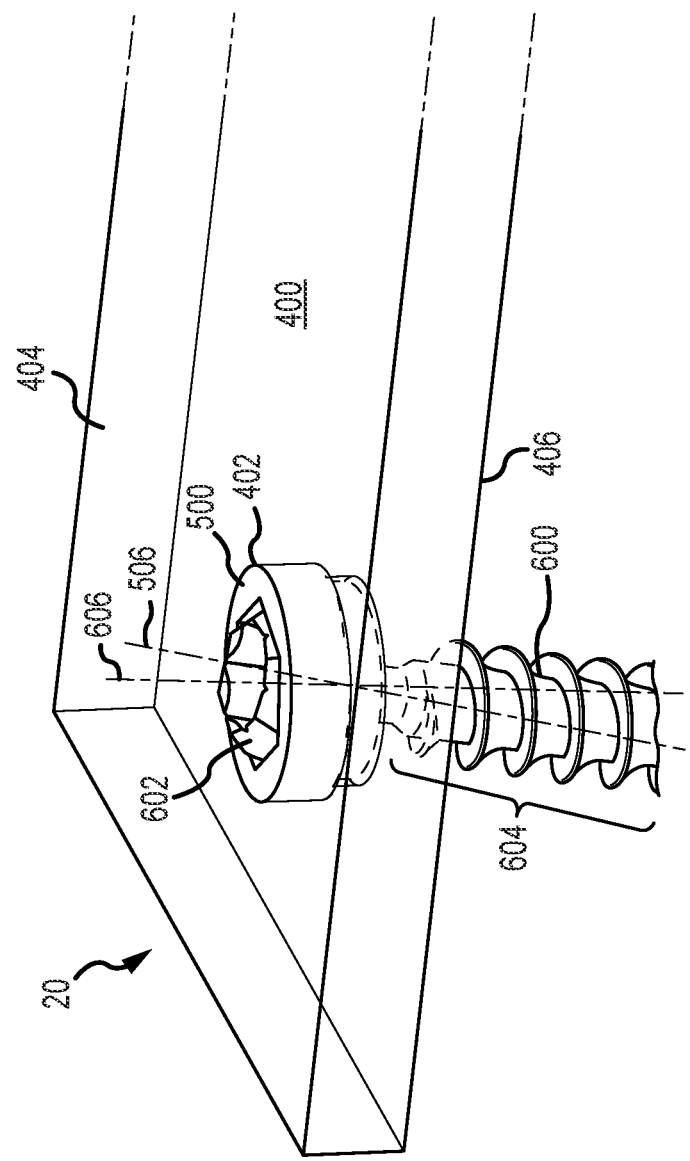
FIG. 11 is a perspective view of an embodiment of an orthopedic implant system in which a plate is shown in phantom for clarity.

FIG. 11 depicts another embodiment of an orthopedic implant system 20. The system 20 includes a plate 400, a pivot member 500, and a fastener 600. Unlike the system 10 described above in which the pivot member 100 is retainedly engaged with the plate 400 within the aperture 202, system 20 may include a fastener 600 that retains the pivot member 500 therewith. In this regard, the pivot member 500 may pivot relative to the fastener 600 and may provide angulation of the fastener 600 while still allowing the pivot member 500 to be lockingly engaged with the plate 400 as will be described in greater detail below.

The plate 400 includes an aperture 402. As shown in FIG. 11, the fastener 600 includes the pivot member 500 in retained engaged relation to a head portion 602 of the fastener 600. In this regard, the fastener 600 may pass through the aperture 402 such that the pivot member 500 engages the plate 400. When engaged with the plate 400, the fastener 600 and pivot member 500 may be lockingly engaged to restrict or prevent movement between the plate 400, pivot member 500 and fastener 600.

Figure 12:
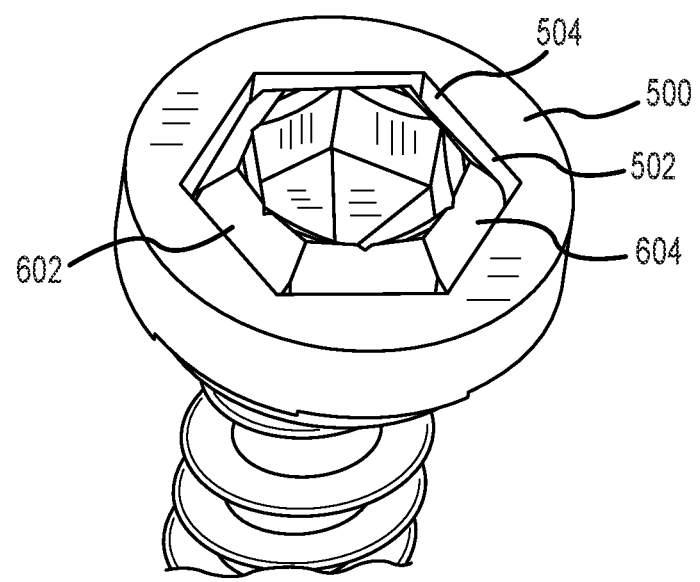
FIG. 12 is a perspective view of an embodiment of a fastener having a pivot member retainedly engaged with a head portion of the fastener.
Figure 17:
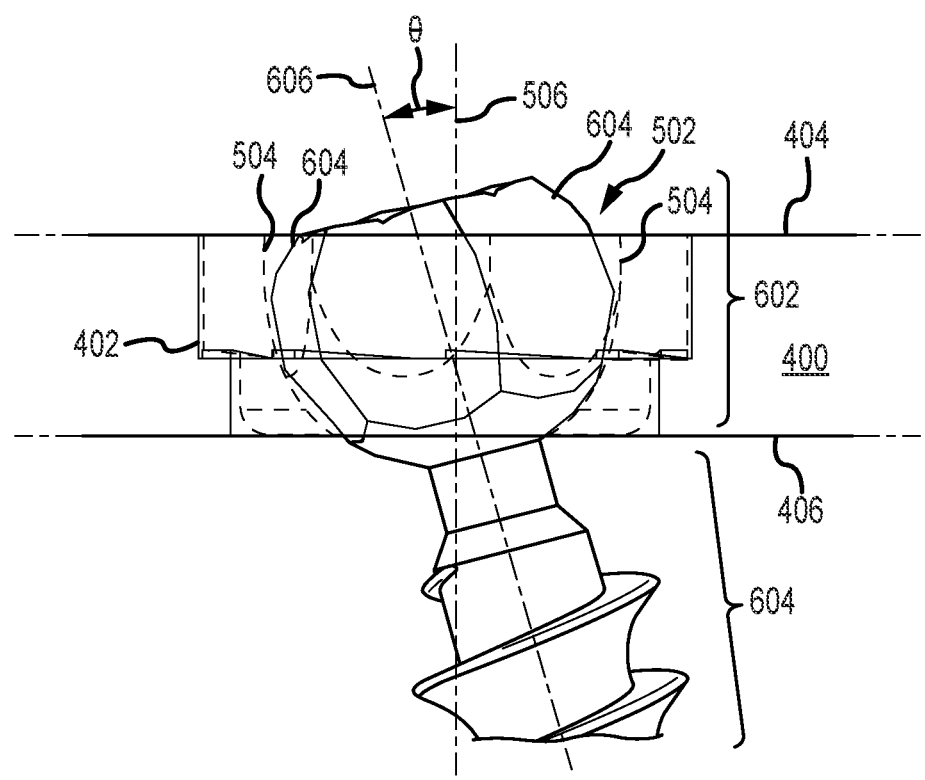
FIG. 17 is a partial cross sectional view of an embodiment of an orthopedic implant system depicting a fastener in locked engagement with a pivot member and plate such that the fastener is disposed at an angle relative to the plate.

With additional reference to FIG. 12, the pivot member 500 may comprise a bore 502. The bore 502 may comprise a non-circular sidewall 504 that at least partially defines the bore 502. The head portion 602 may have an outer surface 604 that is correspondingly non-circular relative to the sidewall 504. In this regard, upon rotation of the fastener 600, the pivot member 500 may undergo corresponding rotational movement by interaction of the sidewall 504 and the outer surface 604. As can best be seen in FIG. 17, the outer surface 604 of the head portion 602 may be in conformal adjacent relation to the sidewall 504 of the bore 502. The outer surface 604 and the sidewall 504 may be curved to allow pivotal movement between the fastener 600 and the pivot member 500. Specifically, the pivot member 500 may define a reference axis 506 about which the bore 502 extends. The fastener 600 may extend along a fastener insertion axis 606. Accordingly, the pivotal movement between the fastener 600 and the pivot member 500 may define an included angle θ therebetween.

The included angle θ in the system 20 may include any of the characteristics described above in relation to system 10. That is, the included angle θ may be defined at any radial position about the reference axis 606. In addition, the included angle θ may be at least about 10 degrees in an embodiment or even at least about 15 degrees.

Figure 13:
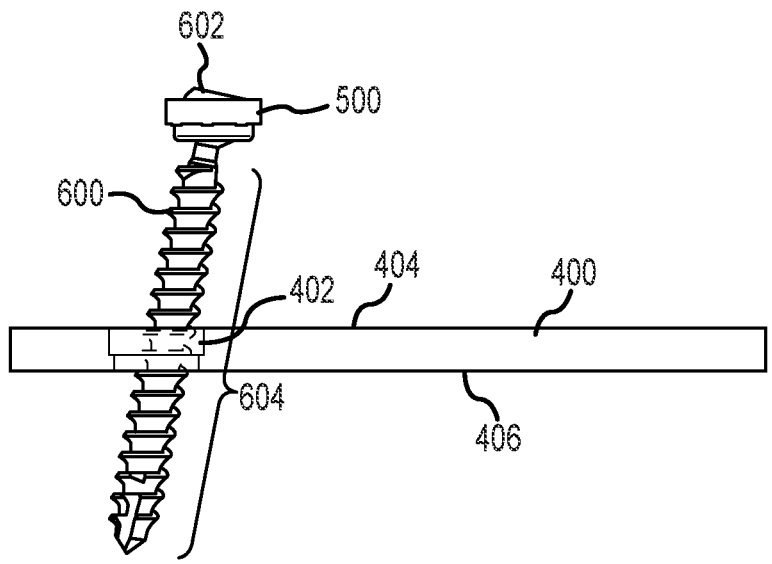
FIG. 13 is a partial cross sectional view of an embodiment of an orthopedic implant system in which a fastener passes through a plate to partially engage a bone of a patient.
Figure 14:
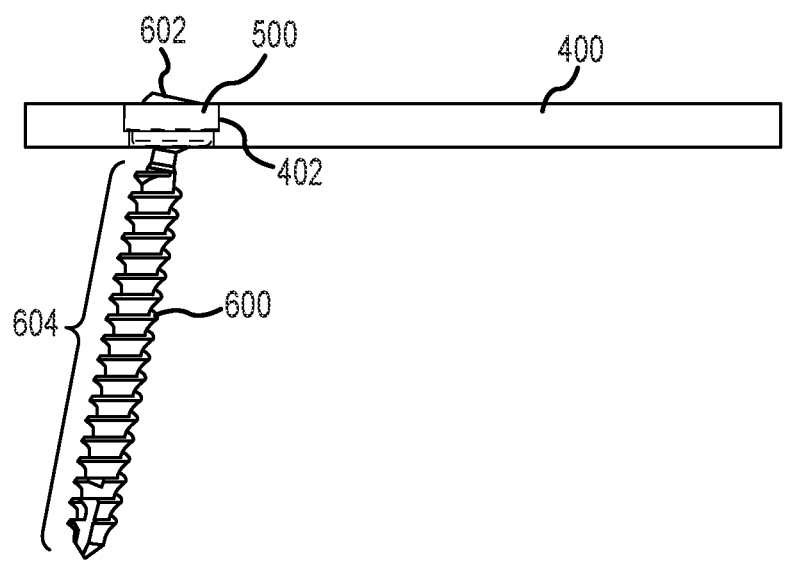
FIG. 14 is a partial cross sectional view of the embodiment of FIG. 13 with the fastener in a fully engaged position.
Figure 15:
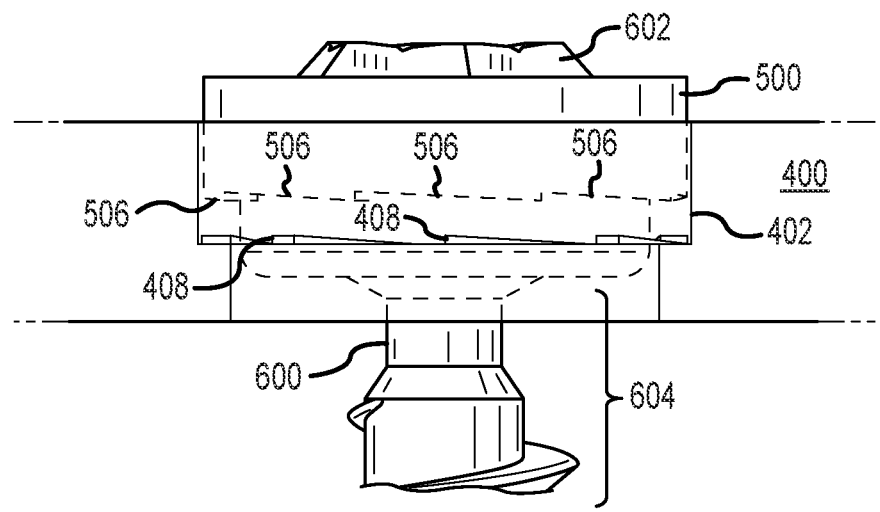
FIG. 15 is a detailed partial cross sectional view of an embodiment of an orthopedic implant system depicting corresponding locking features of a pivot member and a plate in spaced relation prior to engagement therebetween.

With reference to FIG. 13, the fastener 600 may be advanced through the aperture 402 of the plate 400. For instance, while not shown in FIG. 13, the elongate portion 604 of the fastener 600 may be advanced into the bone of a patient. As the fastener 600 is advanced relative to the plate 400, the head portion 602 may be advanced toward the plate 400 such that the pivot member 500 may be disposed within the aperture 402. FIG. 15 shows the fastener 600 is in position such that a portion of the pivot member 500 is disposed with in the aperture 402 of the plate 400.

As can best be seen in FIG. 15, the pivot member 500 comprises a first locking feature on a distal portion thereof. The aperture 402 comprises a second locking feature on a proximal-facing portion of the aperture 402. The first locking feature on the pivot member 500 may correspond to the second locking feature of the aperture 402 so that the first locking feature and the second locking feature are engageable for locking interaction therebetween.

Figure 16:
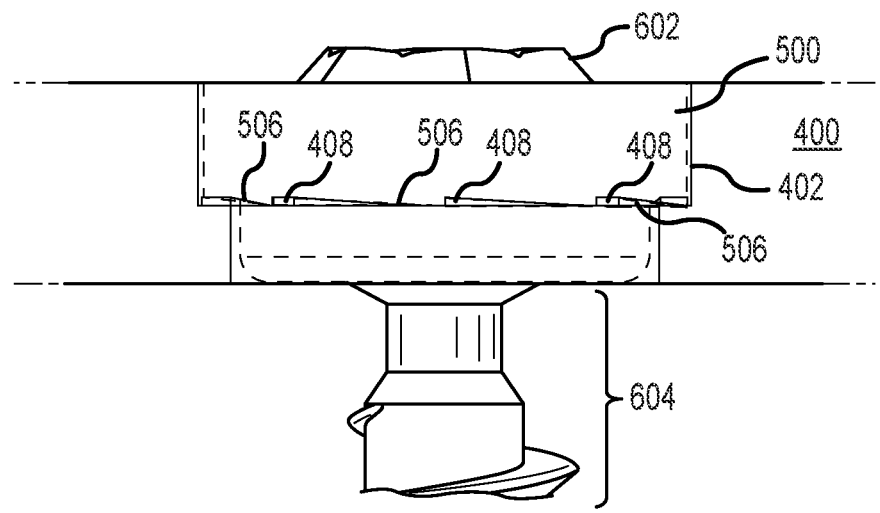
FIG. 16 is a detailed partial cross sectional view of an embodiment of an orthopedic implant system depicting corresponding locking features of a pivot member and a plate in engagement.

Specifically, the first locking feature of the pivot member 500 comprises a plurality of ramped surfaces 506. The second locking feature of the aperture 402 comprises a plurality of teeth 408. As the fastener 600 is advanced relative to the bone of a patient, the fastener 600 also moves distally relative to the plate 400. Because the pivot member 500 is retained by the head portion 602 of the fastener 600, the distal movement of the fastener 600 brings the ramped surfaces 506 in contact with the teeth 408. As the fastener 600 is rotated, the ramped surfaces 506 travel along the teeth 408 in a ratcheting action as the fastener 600 is advanced. Upon continued advancement of the fastener 600, the teeth 408 will interlockingly engage the ramped surfaces 506 as shown in FIG. 16. The interlocking engagement between the ramped surfaces 506 and the teeth 408 may restrict rotation of the fastener 600 in a direction opposite the direction in which the fastener 600 is rotated as it is advanced.

In this regard, as the fastener 600 is advanced relative to the plate 400, the pivot member 500 is clampingly engaged in the aperture 402 by the head portion 602 of the fastener 600. Moreover, the interlocking engagement of the ramped surfaces 506 and the teeth 408 restrict rotation of the fastener 600 tending to withdraw the fastener 600 proximally. As such, the fastener 600 remains clampingly engaged with the plate 400. Moreover, the compressive forces acting between the fastener head 602 and the pivot member 500 create frictional engagement between the outer surface 604 of the head portion 602 and the sidewall 504 of the bore 502. In turn, the included angle θ defined between the fastener insertion axis 606 and the reference axis 506 is maintained as further pivotal movement between the head portion 602 and the pivot member 500 is restricted or prevented based on the frictional interaction between the sidewall 504 and the outer surface 604. By restricted from pivotal movement, it is meant that the forces experienced during bone healing or movement by the patient will not cause such pivotal movement. That is, application of a large force (e.g., by a surgeon with assistance of a tool or the like) may be able to cause such pivotal movement to remove the hardware during a surgical procedure.

Figure 18:
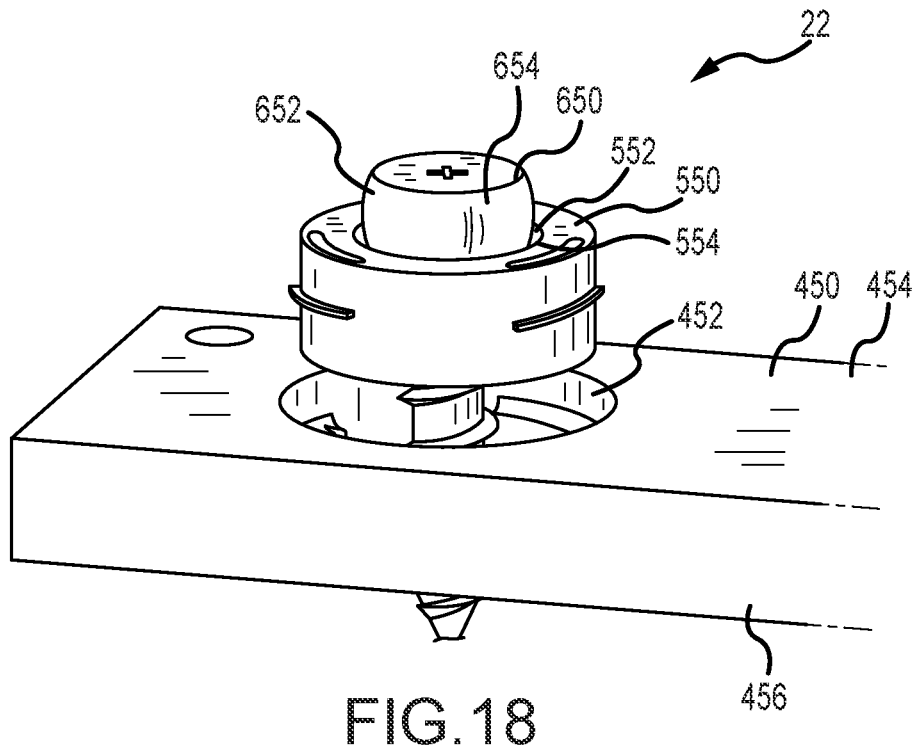
FIG. 18 is a perspective view of an embodiment of an orthopedic implant system in which a fastener is in a partially advanced position relative to a plate.
Figure 19:
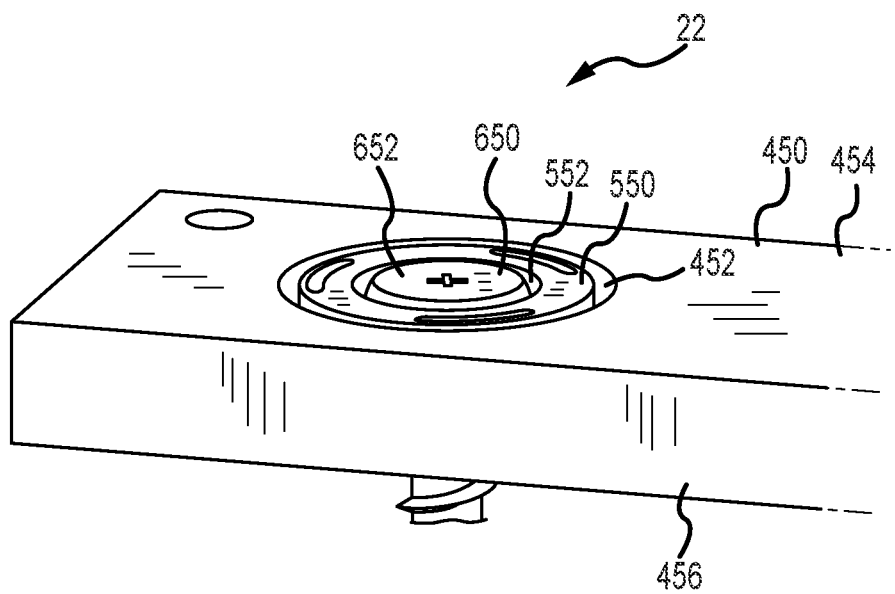
FIG. 19 is a perspective view of an embodiment of an orthopedic implant system in which a fastener is in a fully advanced position relative to a plate.

With further reference to FIGS. 18 and 19, another embodiment 22 of an orthopedic implant system 22 is shown. The system 22 comprises a plate 450, a pivot member 550, and a fastener 650. Like in the embodiment of the orthopedic implant system 20 described above, the pivot member 550 may be retainedly engaged with a head portion 652 of the fastener 600. In this regard, the pivot member 550 may pivot relative to the fastener 650. The pivot member 550 may define a bore 552 that may extend along a reference axis. The fastener 650 may extend along a fastener insertion axis. In turn, the pivotal movement of the pivot member 550 relative to the fastener 650 may define an included angle between the reference axis and the fastener insertion axis as described above in relation to the system 20.

Specifically, the head portion 652 may comprise an outer surface 654. Additionally, the bore 552 may comprise a sidewall 554. The outer surface 654 may be disposed in conforming adjacent relation to the sidewall 554. In the embodiment of the system 22, the outer surface 654 may be arcuate both circumferentially about the fastener insertion axis and at least partially arcuate along the fastener insertion axis. That is, the outer surface 654 may be at least partially spherical. In turn, the sidewall 554 may be conformingly shaped relative to the outer surface 654 such that the sidewall 554 may be at least partially spherical as well. In turn, the pivot member 550 may pivot relative to the head portion 652.

In turn, the fastener 600 may be advanced relative to the plate 450 such that the pivot member 552 is disposed within an aperture 452 of the plate 450 that extends from an upper surface 454 to a lower surface 456 of the plate 450. As can best be seen in FIG. 20, when the pivot member 550 is disposed in the aperture 452, a first locking feature of the pivot member 550 may be disposed relative to a second locking feature of the plate 400. Specifically, the pivot member 550 may comprise a ramped surface 556. This is more clearly seen in FIG. 21, which depicts the position of the pivot member 550 in FIG. 20 without the plate 450 shown for clarity.

Figure 20:
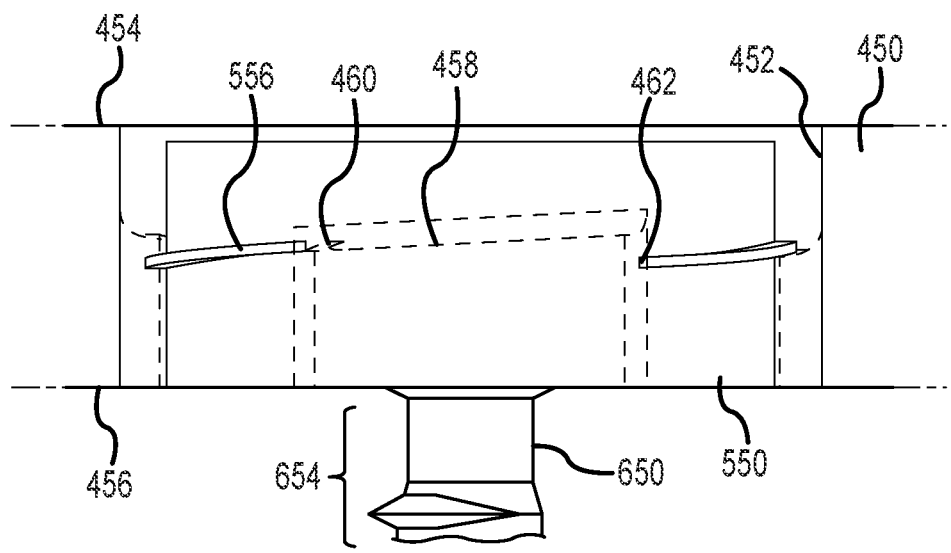
FIG. 20 is a partial cross sectional view of an embodiment of an orthopedic plate system in which a fastener is in a fully advanced position relative to a plate and respective corresponding locking features on a pivot member and plate are disposed in non-locking engagement.
Figure 21:
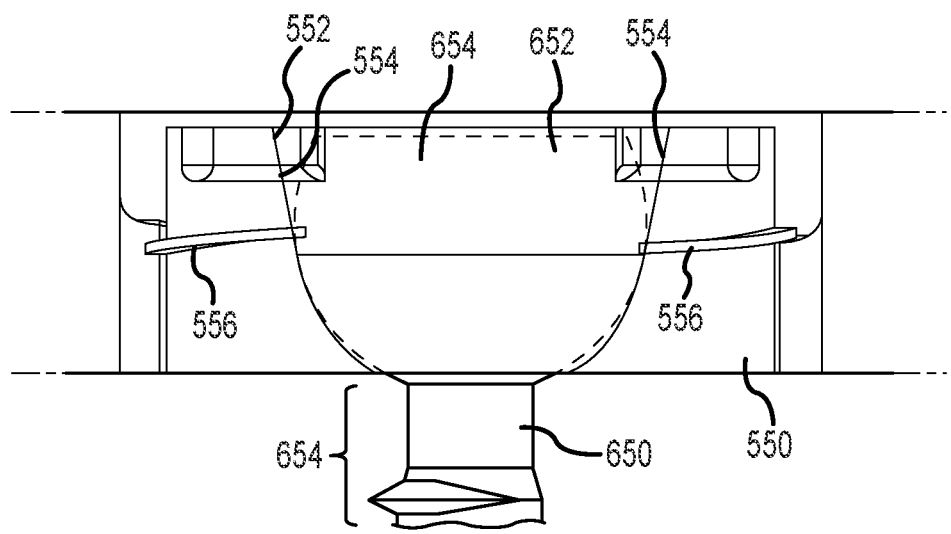
FIG. 21 is a side view of the fastener and pivot member of the embodiment of FIG. 20 shown in isolation for clarity.

As can be appreciated, a plurality of ramped surfaces 556 may also be provided without limitation. The aperture 452 comprises one or more shoulders 458. As such, when the fastener 650 is advanced relative to the plate 450 (e.g., by advancing a threaded elongate portion 654 of the fastener 650 into a bone of a patient), the pivot member 550 that is retained at the head portion 652 may be advanced relative to the aperture 452. The advancement of the fastener 650 may include rotation in a first direction (e.g., clockwise). When the fastener 650 is fully advanced, the pivot member 550 may be disposed such that the ramped surfaces 556 are not contacting the shoulder 458 as shown in FIG. 20.

Figure 22:
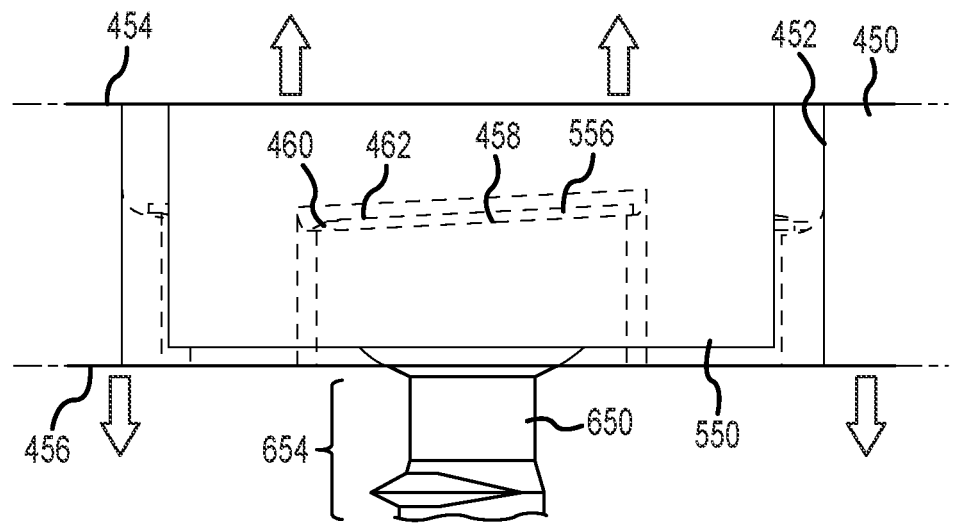
FIG. 22 is a partial cross sectional view of an embodiment of an orthopedic plate system in which a fastener is in a fully advanced position relative to a plate and respective corresponding locking features on a pivot member and plate are disposed in locking engagement.
Figure 23:
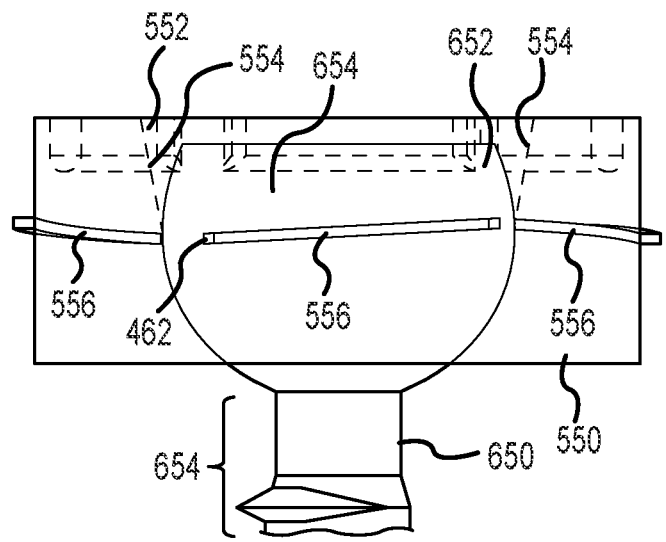
FIG. 23 is a side view of the fastener and pivot member of the embodiment of FIG. 22 shown in isolation for clarity.

In turn, rotation of the pivot member 550 in a second direction opposite the first direction (e.g., counterclockwise) may cause the ramped surfaces 556 to engage the shoulder 458 as shown in FIG. 22. FIG. 23 depicts the position of the pivot member 550 in the absence of the plate 450 for clarity. Specifically, the ramped surfaces 556 may slidingly engage the shoulder 458, which may be inclined in corresponding relation to the ramped surfaces 556. IN turn, the ramped surfaces 556 may slidingly engage to ride up the shoulder 458. This may cause the pivot member 550 to be urged away from the plate 450. As the fastener 650 may be captured in the bone of the patient, the urging of the pivot member 550 away from the plate 450 may clampingly engage the plate 450 with the bone of the patient. Moreover, the pivot member 550 may impart a clamping force on the head portion 652 of the fastener 650. The clamping force acting between the pivot member 550 and the fastener 650 may result in frictional engagement of the sidewall 454 of the aperture 452 with the outer surface 654 of the head portion 652. This frictional engagement may maintain the position of the fastener 650 relative to the pivot member 550.

Additionally, the shoulder 458 may include a lip 460. The lip 460 may be disposed such that a trialing edge 462 of the ramped surface 556 may pass over the lip 460. In this regard, the ramped surface 556 may be disposed relative to the lip 460 such that rotation of the pivot member 550 in the first direction (i.e., tending to cause the pivot member to unclamp the plate 450 and fastener 650) may be restricted by the lip 460. Accordingly, the pivot member 550 may be restricted, and in some instances prevented, from relative movement with respect to the fastener 600. As stated above, restricted relative movement may include prevention of such movement during bone healing or normal patient activities, but could be overcome by the force applied by a surgeon using a tool to remove the fastener 600.

Figure 24:
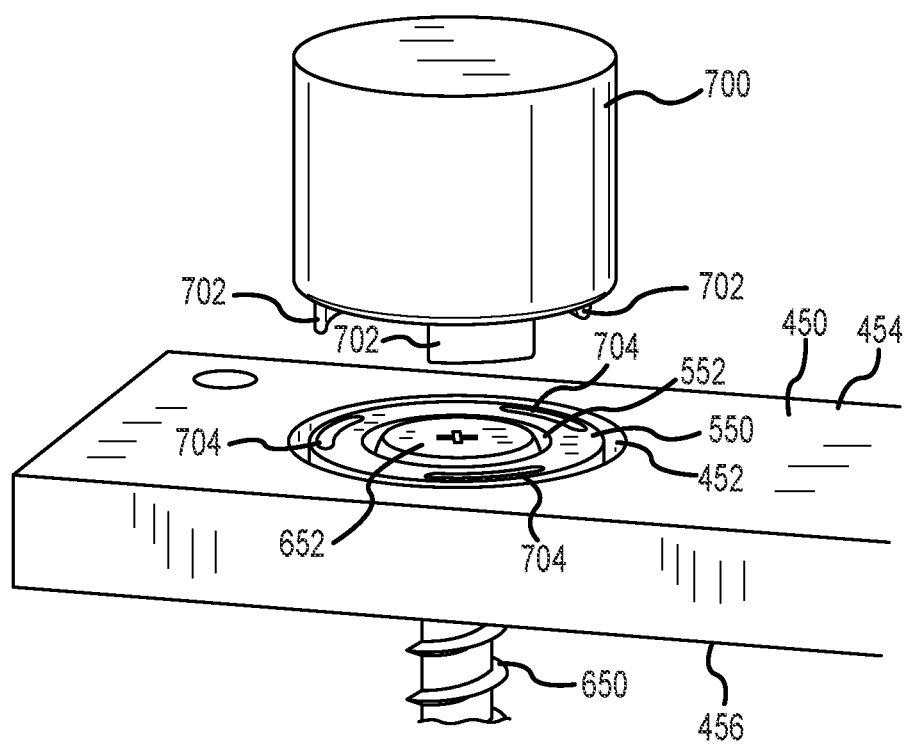
FIG. 24 is a perspective view of an embodiment of an orthopedic plate system in which a tool for disposing a pivot member in locking engagement with the plate is disposed in relative relation to a pivot member.

With further reference to FIG. 24, the rotation of the pivot member 550 in the second direction may be induced by interaction with a tool 700. For instance, the tool 700 may comprise projections 702 that correspondingly engage slots 704 provided on the pivot member 550. In this regard, the tool 700 may be engaged with the pivot member 550 such that the projections 702 engage the slots 704. In turn, the tool 700 may be used to rotate the pivot member 550 to engage the ramped surfaces 556 with the shoulder 458 to impart the clamping forces as described above.

With further reference to FIGS. 25-28, another embodiment of an orthopedic plate system is depicted. The system depicted in FIGS. 25-28 may include a plate 900 having a bore 902 extending from a top surface 904 to a bottom surface 906 of the plate 900. A fastener 850 may be provided that may pass through the bore 902 to engage the bone of the patient for fixation of the plate 900 relative to the bone of the patient. A pivot member 800 may be secured relative to a head portion 810 of the fastener 850. As will be described in greater detail below, the pivot member 800 may be disposed between a head portion 810 and a ledge 814 that extends radially from the fastener 850. In any regard, as the fastener 850 is advanced relative to the bone of the patient, the pivot member 800 may become disposed within the aperture 902 of the plate 900. Thereafter, the pivot member 800 may be selectively radially expanded to lockingly engage the plate 900.

The fastener 850 may include an elongate portion 812. The elongate portion 812 may comprise threads 818 that are engageable with the bone of the patient to advance the fastener 850 relative to the bone of the patient. The fastener 850 may include the head portion 810 which is disposed near a proximal end portion 824 of the fastener 850. The head portion 810 may be threadably engaged with the proximal end portion 824 of the fastener 850. Accordingly, the head portion 850 may be advanced distally or retracted proximally by corresponding respective rotation of the head portion 850 relative to the proximal end portion 824 of the fastener 850. The ledge 814 briefly described above may extend radially relative to a fastener insertion axis 804 that generally extends along the elongate portion 812. The ledge 814 may be extend about the fastener 850 circumferentially such that the ledge 814 defines a stop such that the pivot member 800 may not be advanced distally relative to the ledge 814.

Figure 25:
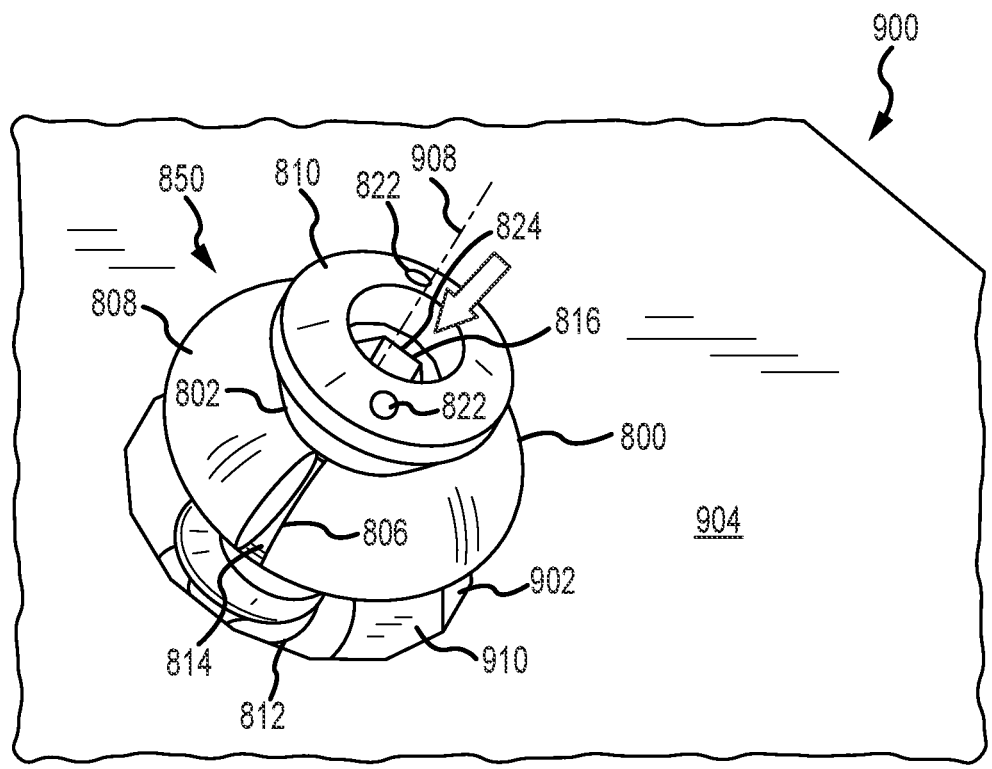
FIG. 25 is a perspective view of an embodiment of an orthopedic plate system with a fastener member partially engage therewith.
Figure 26:
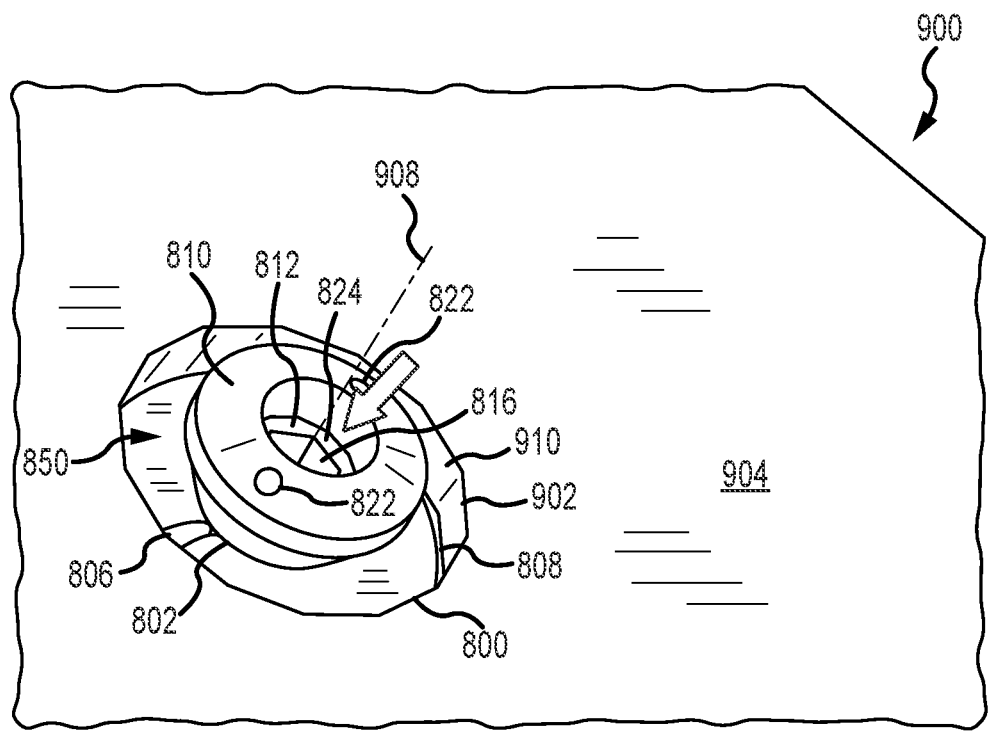
FIG. 26 is a perspective view of an embodiment of an orthopedic plate system with a fastener member advanced with respect thereto.
Figure 27:
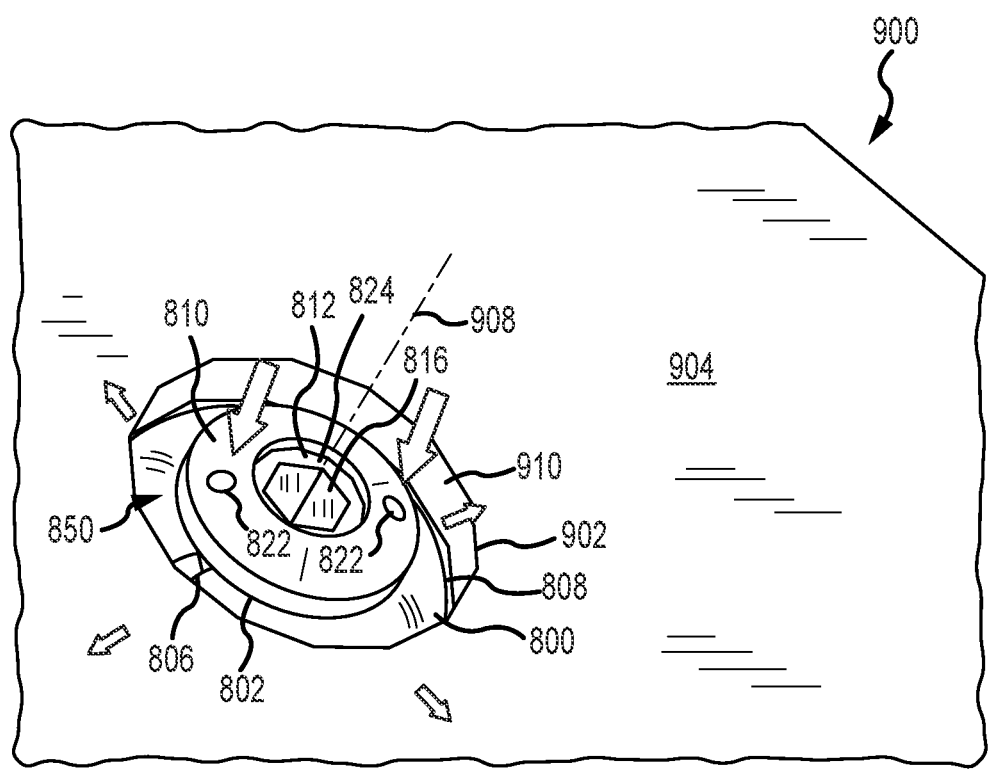
FIG. 27 is a perspective view of an embodiment of an orthopedic plate system with a fastener member advanced with respect thereto and a head portion of the fastener member advanced to lockingly engage the pivot member relative to a plate.
Figure 28:
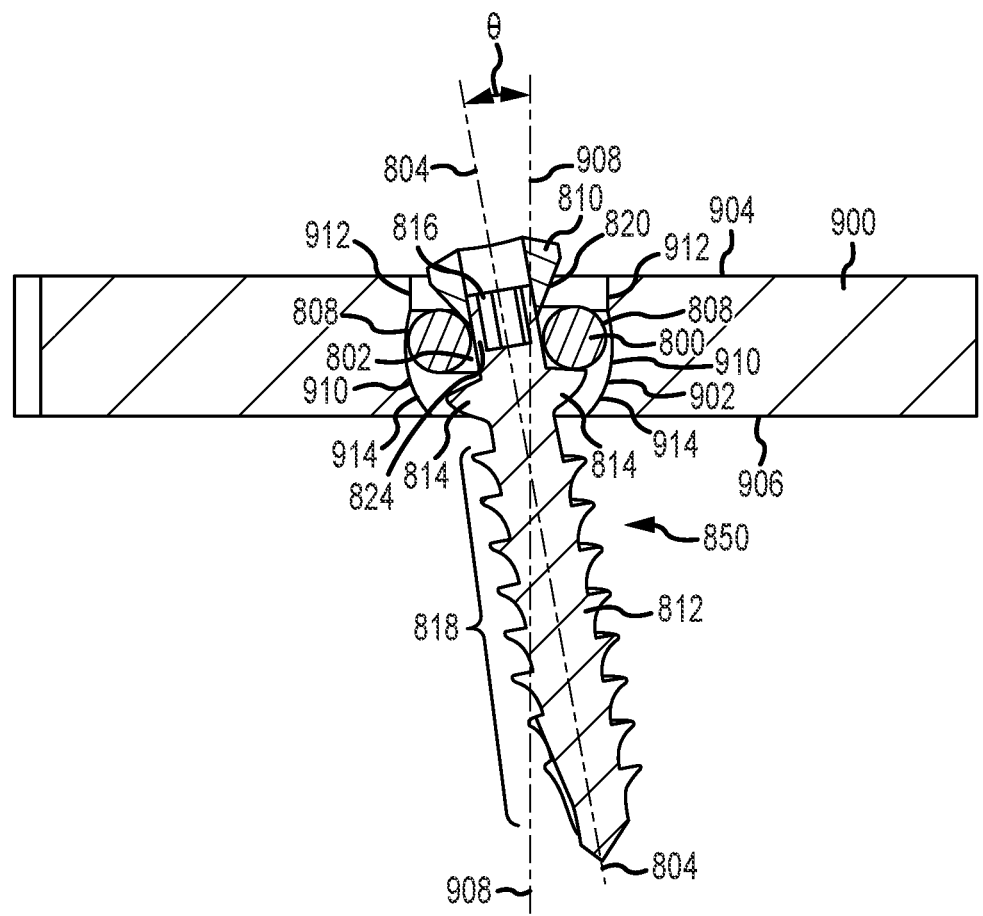
FIG. 28 is a cross sectional view of the embodiment of an orthopedic plate system as shown in FIG. 26 taken along a reference axis of the plate.

As shown in FIG. 25, the pivot member 800 may be arranged such that the pivot member 800 is disposed between the head portion 810 and the ledge 814 to retainedly engaged the pivot member 800 therebetween. As may be appreciated, the pivot member 800 may be relatively easily disposed between the head portion 810 and the ledge 814 by removing the head portion 810 from the proximal end portion 824 of the fastener 850. Thereafter, the pivot member 800 may be disposed about the fastener 850 such that the fastener 850 extends relative to a bore 802 defined by the pivot member 800. The head portion 810 may be reengaged with the proximal end portion 824 by way of the threadable engagement provided therebetween. The engagement of the pivot member 800 relative to the fastener member 850 may be performed prior to a surgeon utilizing the fastener 850 to secure the plate 900 relative to the patient. As such, the fastener 850 with the pivot member 800 disposed relative thereto may be provided for use by a surgeon as an integral unit or preconfigured subassembly such that the utilization of the fastener 850 and pivot member 800 are efficient to the surgeon.

The proximal end portion 824 may include a first tool receiving portion 816. For instance, the first tool receiving portion 816 may comprise a hexagonally shaped recess that may accept a correspondingly hexagonally shaped tool portion. Other configurations of the first tool receiving portion 816 may be provided that allow for controllable rotation of the elongate portion 812 of the fastener 850.

The head portion 810 may include one or more second tool receiving portions 822. For instance, as shown in FIG. 25 the second tool receiving portions 822 may include cylindrical recesses provided in the head portion 810. The second tool receiving portions 822 may be distributed radially about the proximal portion of the head portion 810 such that the second tool receiving portions 822 are accessible from the proximal portion of the fastener 850. It may be appreciated that other configurations of the second tool receiving portions 822 may be provided. Specifically, any configuration that allows for engagement by a tool for controlled rotation of the head portion 810 may be provided without limitation.

In this regard, the first tool receiving portion 816 may be engaged by a tool portion that may in turn impart rotation of the fastener 850 about the fastener insertion axis 804. This may in turn caused threads 818 to engage the bone of the patient and be advanced relative thereto. During the rotational advancement of the fastener 850 the second tool receiving portions 822 may be engaged and correspondingly rotated to prevent relative rotation between the head portion 810 and the proximal end portion 824 of the fastener 850. Alternatively, the first tool receiving portion 816 may be engaged alone to advance the fastener 850. In this regard, the head portion 810 may correspondingly rotate with the proximal end portion 824 absent engagement with the second tool receiving portions 822.

In any regard, as the fastener 850 is advanced relative to the plate 900, the pivot member 800 that may be restrainedly engaged between the head portion 810 and the ledge 814 may also be advanced relative to the plate 900. Specifically, the pivot member 800 may be advanced so that it is disposed within the aperture 902 of the plate 900. The aperture 902 of the plate 900 may include a neck portion 912. The pivot member 800 may also include an expansion slot 806 that allows for radial expansion and contraction of the pivot member 800 relative to the fastener insertion axis 804. In this regard, as the fastener 850 is advanced relative to the plate 900, the pivot member 800 may engage the neck portion 912. Upon further advancement of the fastener 850, the pivot member 800 may be radially compressed such that the pivot member 800 a pass by the neck portion 912 into a pocket 914 of the aperture 902. The pocket 914 may be a spheroid shaped portion comprising a sidewall 910 of the aperture 902. This configuration in which the pivot member 800 is disposed in the pocket 914 of the aperture 902 shown in FIG. 26.

The head portion 810 may be engaged at the second tool receiving portion 822 to impart rotation of the head portion 810 relative to the proximal end portion 824 to advance the head portion 810 distally relative to the proximal end portion 824. As can best be appreciated collectively in FIGS. 27 and 28, the distal advancement of the head portion 810 may cause a ramped surface 820 of the head portion 810 to engage the bore 802 of the pivot member 800. In turn, the distal advancement of the head portion 810 may cause the ramped surface 822 cause the radial expansion of the pivot member 800 such that an outer surface 808 of the pivot member 800 frictionally engages the sidewall 910 of the pocket 914. Accordingly, the pivot member 800 may be lockingly engaged relative to the plate 900 by way of advancement of the head portion 810 relative to the proximal end portion 824 so as to urge the pivot member 800 and radial expansion against the sidewall 910.

As in the previous embodiments, the fastener 850 may be inserted relative to the plate such that an angle θ is included between the fastener insertion axis 804 and the reference axis 908. Upon advancement of the head portion 810 distally relative to the proximal end portion 824 of the fastener 850, the fastener may be lockingly engaged relative to the plate at the angle θ. As in the foregoing embodiments, the angle θ may be at least about 15°.

When utilizing the embodiment depicted in FIGS. 25-28, one or more tools may be provided for engagement of the first tool receiving portion 816 and the second tool receiving portion 822. For example, a single integral tool may be provided that includes a corresponding first tool portion adapted for engagement of the first tool receiving portion 816 and a corresponding second tool portion adapted for engagement of the second tool receiving portions 822. The second tool portion may be movable relative to the first tool portion such that a user may choose to utilize the first tool portion alone, the second tool portion alone, or the first and second tool portions together. That is, the tool may allow for selective engagement of the first, second, and/or first and second tools with the respective tool receiving portion. Alternatively, a discrete first tool having a first tool portion corresponding to the first tool receiving portion 816 may be provided and a discrete second tool having a second tool portion corresponding to the second tool receiving portions 822 may be provided. In this regard, the first tool may be utilized to advance the fastener 850 into the position shown in FIG. 26. The first tool may be disengaged from the first tool receiving portion 816. The second tool may then be engaged with the second tool receiving portions 822 to rotate the head portion 810 relative to the proximal end portion 824 to distally advance the head portion 810 causing radial expansion of the pivot member 800.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. An orthopedic fastener assembly for use in fixation of an orthopedic plate to a bone of a patient, the assembly comprising:
    a fastener comprising:
        an elongate portion on a distal portion of the fastener comprising threads for engagement with a bone of a patient, and
        a non-circular head portion at a proximate portion of the fastener; and
    a pivot member comprising a bore defining a reference axis and having a non-circular contoured surface disposed about and pivotally displaceable relative to the head portion for pivotal articulation of the pivot member about the head portion, the pivot member comprising a first locking feature to lockingly engage the pivot member to the orthopedic plate through which the fastener has been advanced, the fastener extending along a fastener insertion axis, wherein prior to an engagement with the orthopedic plate, the pivot member is moveable relative to the head portion and secured thereto to prevent removal of the pivot member from the head portion, and wherein the pivotal articulation of the pivot member about the head portion defines an included angle between the reference axis and the fastener insertion axis;
    wherein the non-circular contoured surface and the non-circular head portion interface to restrict rotation of the pivot member about the fastener insertion axis.

2. The orthopedic fastener assembly of claim 1, wherein the included angle between the reference axis and the fastener insertion axis is definable at any radial position about the reference axis.

3. The orthopedic fastener assembly of claim 2, wherein the included angle is at least about 10 degrees.

4. The orthopedic fastener assembly of claim 3, wherein the included angle is at least about 15 degrees.

5. The orthopedic fastener assembly of claim 1, wherein the first locking feature corresponds to and is engageable with a second locking feature on the orthopedic plate through which the fastener is advanceable.

6. The orthopedic fastener assembly of claim 5, wherein the first locking feature comprises a ramped surface engageable with corresponding teeth on the orthopedic plate through which the fastener is advanceable to allow for rotation of the pivot member in a first direction relative to the plate and to restrict rotation in a second direction opposite the first direction when the ramped surface engages the corresponding teeth on the plate.

7. The orthopedic fastener assembly of claim 1, wherein the first locking feature comprises a ramped surface engageable with a corresponding shoulder on a sidewall of an aperture extending through a plate through which the fastener is advanceable, wherein the ramped surface is rotationally displaceable relative to the shoulder to lockingly engage the pivot member relative to the plate.

8. The orthopedic fastener assembly of claim 7, wherein the bore of the pivot member comprises a sloped surface extending away from the reference axis in a proximal direction, and coordinated engagement of the ramped surface and the shoulder urges the pivot member proximally to lockingly engage the pivot member relative to the plate in response to rotation of the pivot member in a first rotational direction.

9. The orthopedic fastener assembly of claim 8, wherein the shoulder comprises a lip for coordinated engagement of a trailing edge of the ramped surface to restrict rotation of the pivot member in a second rotational direction opposite the first rotational direction.

10. An orthopedic fastener assembly for use in fixation of an orthopedic plate to a bone of a patient, the assembly comprising:
a fastener comprising:
   an elongate portion on a distal portion of the fastener comprising threads for engagement with a bone of a patient, and
   a head portion at a proximate portion of the fastener; and
a pivot member comprising a bore defining a reference axis and having a contoured surface circumferentially arcuate about the bore and disposed about and pivotally displaceable relative to the head portion for pivotal articulation of the pivot member about the head portion, the pivot member comprising a first locking feature comprising a ramped surface to lockingly engage the pivot member to a second locking feature comprising a shoulder on a sidewall of an aperture through the orthopedic plate through which the fastener has been advanced, the ramped surface rotationally displaceable relative to the shoulder to lockingly engage the pivot member relative to the plate,
wherein prior to an engagement with the orthopedic plate, the pivot member is rotatable about the head portion about a fastener insertion axis and secured thereto to prevent removal of the pivot member from the head portion, and
wherein the pivotal articulation of the pivot member about the head portion defines an included angle between the reference axis and the fastener insertion axis.

11. The orthopedic fastener assembly of claim 10, wherein the included angle between the reference axis and the fastener insertion axis is definable at any radial position about the reference axis.

12. The orthopedic fastener assembly of claim 10, wherein the bore of the pivot member comprises a sloped surface extending away from the reference axis in a proximal direction, and coordinated engagement of the ramped surface and the shoulder urges the pivot member proximally to lockingly engage the pivot member relative to the plate in response to rotation of the pivot member in a first rotational direction.

13. The orthopedic fastener assembly of claim 12, wherein the shoulder comprises a lip for coordinated engagement of a trailing edge of the ramped surface to restrict rotation of the pivot member in a second rotational direction opposite the first rotational direction.

\* \* \* \* \*